(12) United States Patent
Zhu et al.

(10) Patent No.: US 8,969,061 B2
(45) Date of Patent: Mar. 3, 2015

(54) COMPOSITIONS, METHODS AND RELATED USES FOR CLEAVING MODIFIED DNA

(75) Inventors: Zhenyu Zhu, Beverly, MA (US); Yu Zheng, Topsfield, MA (US); Shengxi Guan, Stoneham, MA (US); Hua Wang, Topsfield, MA (US); Aine Quimby, Newton, NH (US); Penghua Zhang, Lexington, MA (US); Lynne Apone, Waltham, MA (US)

(73) Assignee: New England Biolabs, Inc., Ipswich, MA (US)

( * ) Notice: Subject to any disclaimer, the term of this patent is extended or adjusted under 35 U.S.C. 154(b) by 120 days.

(21) Appl. No.: 13/522,224

(22) PCT Filed: Jan. 20, 2011

(86) PCT No.: PCT/US2011/021879
§ 371 (c)(1),
(2), (4) Date: Jul. 13, 2012

(87) PCT Pub. No.: WO2011/091146
PCT Pub. Date: Jul. 28, 2011

(65) Prior Publication Data
US 2012/0301881 A1    Nov. 29, 2012

Related U.S. Application Data

(60) Provisional application No. 61/376,932, filed on Aug. 25, 2010, provisional application No. 61/296,630, filed on Jan. 20, 2010.

(51) Int. Cl.
C12Q 1/00 (2006.01)
C12Q 1/68 (2006.01)
C12Q 1/34 (2006.01)
C12N 9/00 (2006.01)
C12N 9/22 (2006.01)

(52) U.S. Cl.
CPC ............... *C12N 9/22* (2013.01); *C12Q 1/6827* (2013.01)
USPC ....... 435/199; 435/4; 435/6; 435/18; 435/183

(58) Field of Classification Search
None
See application file for complete search history.

(56) References Cited

U.S. PATENT DOCUMENTS

| 5,643,758 A | 7/1997 | Guan et al. |
| 5,670,637 A | 9/1997 | Gold et al. |
| 5,693,502 A | 12/1997 | Gold et al. |
| 5,696,249 A | 12/1997 | Gold et al. |
| 5,874,557 A | 2/1999 | Gold et al. |
| 7,141,366 B1 | 11/2006 | Sandman et al. |
| 7,825,218 B2 | 11/2010 | Riggs et al. |
| 7,939,284 B2 | 5/2011 | Johnsson et al. |
| 2012/0156677 A1* | 6/2012 | Bitinaite et al. ............. 435/6.11 |

FOREIGN PATENT DOCUMENTS

| JP | 5 244946 A | 9/1993 |
| WO | WO 2010/037001 | 4/2010 |
| WO | WO2010/075375 | 7/2010 |
| WO | WO 2010/114532 | 10/2010 |
| WO | WO 2011/025819 | 3/2011 |

OTHER PUBLICATIONS

Janosi, et al., Journal of Molecular Biology, 242, 1, 45-61, 1994.
Databse UniProt, "sSubName: Full=Restriction endonuclease PvuRTs1I;", Nov. 24, 2009.
Szwagierczak, et al., Nucleic Acids Research, 38, 19, 2010.
Tahiliani et al., Science 324(5929): 930-5 (2009).
Kriaucionis, et al., Science 324(5929): 929-30 (2009).
Cokus et al., Nature 452: 215-219 (2008).
Pei, et al., Bioinformatics 23(7):802-808 (2007).
Ishaq, et al., Biological Chemistry 255(9):4040-4047 (1980).
Janosi, et al. Biophysical Journal. 61(2 Part 2): A216 (1992).
Murata et al. Journal of Bacteriology 184(12):3194-202 (2002).
Song et al. Nature Biotechnology 29: 68-72 (2011).
Zhang et al. J. Comput. Biol. 7(1-2): 203-214 (2000).
International Search Report for International Application No. PCT/US2011/021879.
Gi, et al., Nucleic Acids Research, 38, 11, e125, 2010.

* cited by examiner

*Primary Examiner* — Suzanne M Noakes
*Assistant Examiner* — Jae W Lee
(74) *Attorney, Agent, or Firm* — New England Biolabs, Inc; Harriet M. Strimpel

(57) ABSTRACT

Compositions, methods and a kit are described relating to a novel family of enzymes which preferentially bind to a hydroxymethylated cytosine or a glucosylated hydroxymethylated cytosine and cleave double-stranded DNA at a defined distance 3' of the recognition site to produce a cleavage fragment with a 1-3 base overhang.

13 Claims, 18 Drawing Sheets

FIG. 2
(SEQ ID NO: 1)

```
  1  TTTTAAATTA AAAATGAAGT TTTAAATCAA TCTAAAGTAT ATATGAGTAA
 51  ACTTGGTCTG ACAGTTACCA ATGCTTAATC AGTGAGGCAC CTATCTCAGC
101  GATCTGTCTA TTTCGTTCAT CCATAGTTGC CTGACTCCCC GTCGTGTAGA
151  TAACTACGAT ACGGGAGGGC TTACCATCTG GCCCCAGTGC TGCAATGATA
201  CCGCGAGACC CACGCTCACC GGCTCCAGAT TTATCAGCAA TAAACCAGCC
251  AGCCGGAAGG GCCGAGCGCA GAAGTGGTCC TGCAACTTTA TCCGCCTCCA
301  TCCAGTCTAT CAATTGTTGC CGGGAAGCTA GAGTAAGTAG TTCGCCAGTT
351  AATAGTTTGC GCAACGTTGT TGCCATTGCT ACAGGCATCG TGGTGTCACG
401  CTCGTCGTTT GGTATGGCTT CATTCAGCTC CGGTTCCCAA CGATCAAGGC
451  GAGTTACATG ATCCCCCATG TTGTGCAAAA AAGCGGTTAG CTCCTTCGGT
501  CCTCCGATCG TTGTCAGAAG TAAGTTGGCC GCAGTGTTAT CACTCATGGT
551  TATGGCAGCA CTGCATAATT CTCTTACTGT CATGCCATCC GTAAGATGCT
601  TTTCTGTGAC TGGTGAGTAC TCAACCAAGT CATTCTGAGA ATAGTGTATG
651  CGGCGACCGA GTTGCTCTTG CCCGGCGTCA ATACGGGATA ATACCGCGCC
701  ACATAGCAGA ACTTTAAAAG TGCTCATCAT TGGAAAACGT TCTTCGGGGC
751  GAAAACTCTC AAGGATCTTA CCGCTGTTGA GATCCAGTTC GATGTAACCC
801  ACTCGTGCAC CCAACTGATC TTCAGCATCT TTTACTTTCA CCAGCGTTTC
851  TGGGTGAGCA AAAACAGGAA GGCAAAATGC CGCAAAAAAG GGAATAAGGG
901  CGACACGGAA ATGTTGAATA CTCATACTCT TCCTTTTTCA ATATTATT
```

FIG. 8C
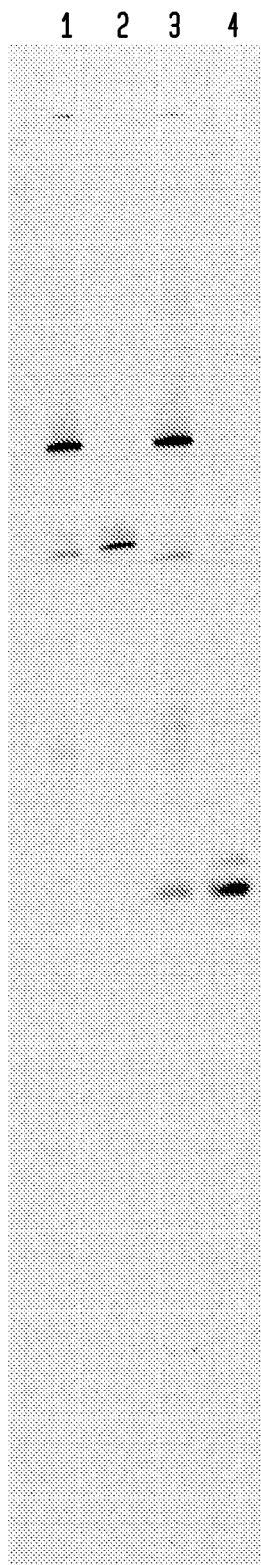
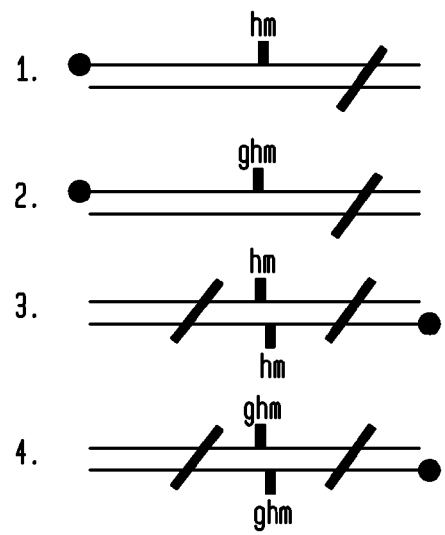

FIG. 13-1

```
Conservation:          5   7 9765  9 9 956557 7 75    56 5699 6           7 99 795
BmeDI          1 M------NKYDYIKRQLAKTMKNQDENYIVTRIWHLLDNYDIKINTQQYVRSMKNQKAEYGLIDLYFPQ    64
BbiDI          1 MS-----GADKLGYLIRALSRLRKRDYENYVVNALWNRLAMDDVKPVTQQLVLMPD--G--RRSPVDLYFPQ   63
AbaSDFI        1 MCNKASSDLTDYVIRQLGRPTMNKRYEAYVVSRIIHLLNDFTLKFVTQQFVRLSN--K--KIALTDLYFPQ   66
PatTI          1 M------DKKEYIIRQLGRTMKKYEAYVVTRIIHLLNDFSIKFITQQYVTRPK--G--RALTDLYFPQ     59
YkrI           1 M------ISQYEYVVRQLARTMKHEQYVVTGIVHKLMRDDIKFVTQQYVKRES--G--RALTDLYFPA     60
SpeAI          1 M------KTLHWTRQLQRCKNKRFELYAITRITHKVDDLDLKFITQQYVARPD--G--FALTDLYLPQ     58
EsaNI          1 MS-----KFTKETYVTRNFQKISGKRWELYITRVIHLLNDPDIEYVCQQYINPPQNKD--YYLADLAPPS   64
PpeHI          1 M------SKTDYILRSLSKITKKRWEHYVINRIFHKLDDPEIEFVCQQCIRKANSPD--KIYLADLFPQ   62
PvuRts1I       1 M------SKTDYILRALSKISHKRWEHYIINRVVHTLDDPDIEFVCQQCIRKEGHLG--KIYLADLFPQ   62
Consensus_ss:                hhhhhhhhhhhhhhhh         hhhhhhh              hhhhhh Conservation:        5 59599  9               9 9 59 5          56  77 6
BmeDI         65 PNLAVEIDEAHHKNDIN------QTLDEIRKNDIVNA-----LDCEFIRIDATQ---- 107
BbiDI         64 AMIGVECDEAYHQRQ--------RERDRERELTTDVLRQIRGEDYRALHVDVSG---- 110
AbaSDFI       67 LGIHIEVDEGHHFLRNSKMEYSLNQIDEPLYSISQTESDAMREEDIISI------TGHKIFRVNVFKNQE 130
PatTI         60 FAFHIEVDEGQHFNQAN------IEADKIREADIINA-----TGHEILRIDVTK---- 102
YkrI          61 INLHIEIDEPFHLKQ--------AEHDNLREADIIDA-----TGHEVIRISVDG---- 101
SpeAI         59 LKLHIEIDEGFHKQQ--------VDADKVRELDIITA-----TDHQVKRIDASV---- 99
EsaNI         65 LKLYLEIDEGQHGSEMH------QTSDLKRDAEILEA-----TDWTCKRIPVFVKKG 110
PpeHI         63 LALYLEIDEEHHDSDEA------KKDAKRRLDIIEA------TGFIEKRIPASN--- 105
PvuRts1I      63 LNLYLEIDEAHHDSNDA------RKADAVRRLDIVEA-----TGFQEERIPASN--- 105
Consensus_ss:       eeeeee h  hhh            hhhhhhhhhhhhhh     eeeeee
```

FIG. 13-2

```
Conservation:       5  79  7   5            5  7 97 5           5   555 6   75
BmeDI      108 ------SPEKIHEKIDQVVEKINL----LTKEKWFIPWDLEKEYDPNTYIEQ-GYIDADDNVSLRLVADC 166
BbiDI      111 ------SYEQVERSIDDCVRRIRAEIERRRQANEFTPW-TEAYVDYKEFYKTRDAVSVADDVGFPRIADA 173
AbaSDFI    131 GQ--PQNLENIHQQIDKIIEEIKTAKNKLTEASTFKEWNIETEYNPQTYIDL-GRISLADNVVLKTTKDV 197
PatTI      103 ------SFDDINTQIDAAVNKIKSMRQEI-----SFIPWDIDSEFDSATYIKR-GYIDIKDNVAFKTIKDA 161
YkrI       102 ------SLRQMNERIDDCVAAIKSKISALGD--CFEPWMDKELSIEPHIRR-GYIDVKDNVAFPRITDA 162
SpeAI      100 ------AIEQINLQVDQIVAEILQSVEVQKQMVSAGHKISWNYEQKFSPDTFIAK-EKIKVSDNVALNHRDV 162
EsaNI      111 SSKIDKSLEALNKEIDDFVSYVEQKQMVSAGHKISWNYEQKFSPDTFIAK-EKIKVSDNVALNHRDV 179
PpeHI      106 ------VTIEQLNTSIDEFVLLIDTKEKQKFTPWDYSAQTAKRHIDA-GFIEVGPHAIFRYHRDA 169
PvuRts1I   106 ------ITLSEVNKLVDEFVRLVDKKEELENQGLFFRWDYDERYSAKKHINT-GYMAVGPNSVFRYHRDA 169
Consensus_ss:          hhhhhhhhhhhhhhhhh      e       hhhhh  ee     hhhhhhhh Conservation:   5  77       7 55 6   7              5757775  5           9 9 55 55  77
BmeDI      167 CNVFGAGYAHGIQKSG-APHKFE------EDTDIKRLKFPPNET----WNNQLLENEEIFIEYNTI-  221
BbiDI      174 VNTLCGSEYKRPQES--WFVPSVMRQWYG-DRYRVWFPKLAIGGKAVANGWNNRLSDDGTYIYEYNED- 238
AbaSDFI    198 CNCFGYSY--KNYQRGG-ALHPYK------KDTLLWFPPRLYENKD----WINTISPDGLTITEKSTD- 251
PatTI      162 CNCFGHNY-TGYQRAG-AAHPD--------HYIMLNFPKLFPNGE----WDNQISSDEEVITERNED-  214
YkrI       163 CNCFGHNY-KFLQKAG-AKHPYH-------DDILIWLPKLFDNEH----WSNQISNDENVITEIPKS-  216
SpeAI      163 CNILGHNY-KGWQRSS-ASVPHY-------PNIRLMFPKLYPNEQ----WTNHISYDGCEIHEYCIE-  216
EsaNI      180 LRLFGYKK-GHYQRAV-WTIKKT-------NQAVWFPKLYPNSD----WVNSFPDDKSGYIHQFRKDN 233
PpeHI      170 LECFGYIN-KGHHQSGSWKLPENIVREIGLSGRIMVWFPPRLYNAGV--WNNELSPDGEWITEESLE-  232
PvuRts1I   170 LQCFGYRR-EGHHQSGGWALPAEVAQSIGLTGRVMVWFPPRLYEAGE----WKNALSADGNKITEQSLN- 232
Consensus_ss:  hhh                            eeeeee                        eeee
```

FIG. 13-3

```
Conservation:                          55 579 5          759 9 6   5       5 96 5
BmeDI        222 PEEN--EAYFQKRM-----YQLN-QKIALFAYAKTSSG-RFEAIFKGLYLLNREKSKNTGVLTYNRISTIMP 284
BbiDI        239 ADLVD-PVGDG--------DPND-IRI-TFAKSADPVTRIQAYRFVGVFRISNSEDG-TRKRYQRIETVFP 298
AbaSDFI      252 ETITL-KKLEEWK------NGPQ-KRI-VFARVKDNLSSRAMYRFMGLYEFQKADLKD--GAVWKRVKCEVQ 312
PatTI        215 DKKAK-QHVSSHVNNKEKHKH-QRI-VFAKVRGNLG-DVLYRFRGQYQLDVKDSNEKTGLIWRIKTRVK 280
YkrI         217 EDAQA-AHFDKWMA-----ETRN-KRL-VFAKAKDNLG-MTLYRFKGLYELNPKKSNRTIGLYWQRISTRVK 279
SpeAI        217 SETKKRQFIDKNL------SENI-QQM-VFARVKDELG-QTMYRFKGLFILDRDKTCHESGVYWKVATEFE 279
EsaNI        234 QPHPM---------P----KEGDPDRI-VFAHQKNIFG-QTVYKFPGIFRADLNKTDPVHH--YFKRINTCLD 289
PpeHI        233 VDNNY------I------EDWD-YRI-VMAHSRDELN-RVLYRFLGVPQIDKNKSVEGKN--IFKRINTKVK 287
PvuRts1I     233 ATRNY------Q------ETWD-YRI-VMAHSRDELN-RTLYRFLGVFAIDVDKSSDEVK--VFSRVYSRVN 287
Consensus_ss:    hhhhh hhhhhh                 ee eeeee hhh hhhhhh eeeee          eeeeeee ee Conservation:
BmeDI        285 TYYP-KDVKQPLRIARAYNNDEYKVAHFYTENQVRKFEGKYKKKRYKIISYS 334   (SEQ ID NO: 5)
BbiDI        299 IHRTPC-------------LPIHR------------------------ 309   (SEQ ID NO: 6)
AbaSDFI      313 TYSPK--------------ETKC------------------------ 321   (SEQ ID NO: 7)
PatTI        281 TYEQN------------------------------------------ 285   (SEQ ID NO: 8)
YkrI         280 TYPSPA-------------RNPD------------------------ 289   (SEQ ID NO: 9)
SpeAI        280 LGLT------------------------------------------- 283   (SEQ ID NO: 10)
EsaNI        290 LSRYSA-------------N--------------------------- 296   (SEQ ID NO: 11)
PpeHI        288 VFNSYN----------------------------------------- 293   (SEQ ID NO: 12)
PvuRts1I     288 VYRSQN----------------------------------------- 293   (SEQ ID NO: 13)
Consensus_ss:    ee
```

COMPOSITIONS, METHODS AND RELATED USES FOR CLEAVING MODIFIED DNA

CROSS REFERENCE

This application is a §371 application of international application number PCT/US2011/021879 filed on Jan. 20, 2011, which claims priority from U.S. provisional application No. 61/296,630 filed Jan. 20, 2010, and 61/376,932 filed Aug. 25, 2010, herein incorporated by reference.

BACKGROUND

Recently, it has been speculated that a 5-hydroxymethyl cytosine (hmC) plays a role in mammalian gene expression, specifically in embryonic stem cells and neuronal cell development as an intermediate step in demethylation (Tahiliani et al., Science 324(5929): 930-5 (2009); Kriaucionis and Heintz, Science 324(5929): 929-30 (2009)). A TET family of enzymes has been described that catalyzes the conversion of 5-methylated cytosine (mC) to hmC (WO 2010/037001). Detection of hydroxymethylation has proved challenging. Chemical methods, most commonly sodium bisulfite sequencing used to detect mC, do not discriminate between mC and hmC (Cokus et al., Nature 452: 215-219 (2008). PCT Publication No. WO 2010/037001 describes the use of antibodies that bind directly to hmC. A product that includes mixtures of endonucleases allows detection of hmC by subtraction (EpiMark™, New England Biolabs, Inc. (NEB) and PCT/US10/46632). This product utilizes T4 β-glucosyltransferase (BGT) to glucosylate the hmC which is then resistant to endonuclease cleavage permitting differentiation from mC. It would be desirable to develop simple rapid and direct methods to detect and analyze the presence of hmC in a polynucleotide sequence context which additionally are capable of discriminating hemi-hmC from symmetric hmC so as to precisely identify the cytosine (C) that is hydroxymethylated.

SUMMARY

In an embodiment of the invention, a preparation is provided that includes: one or more purified recombinant proteins wherein the proteins are members of a family of ZZYZ proteins; and a reaction buffer. In embodiments of the invention, each member of the family of ZZYZ proteins have a catalytic domain and a binding domain. In an embodiment, the binding domain preferentially binds to hmC and to a glucosylated hydroxymethylated cytosine (ghmC) in a DNA. In an embodiment, the catalytic domain cleaves DNA at a defined distance (3') from the hmC or ghmC. The defined distance may be further characterized as 11-13 nucleotides on the strand having the hmC or ghmC and 9-10 nucleotides on the complementary strand (3'). Each member of the family of ZZYZ proteins may be further characterized by its recognition of a modified nucleotide selected from ghmC or hmC in a DNA such that the ratio of cleavage is at least 8:1 of ghmC or hmC to mC.

In an embodiment of the invention, each member of the family of ZZYZ proteins has an N-terminal domain comprising an amino acid sequence with at least 95% amino acid sequence homology with $RX_7KX_2EXYX_{18}QQX_{11-16}DLX_2PX_6EXDEX_2HX_{6-26}DX_2RX_3I$ (SEQ ID NO:14). In another embodiment, each member of the family of ZZYZ proteins has a C-terminal domain comprising an amino acid sequence with at least 95% amino acid sequence homology with $WXNX_{30-40}AX_{12-13}FXGX_{16-18}R$ (SEQ ID NO:15) in the C-terminal domain. In a further embodiment, at least one member includes the amino acid sequence $RX_7KX_2EXYX_{18}QQX_{11-16}DLX_2PX_6EXDEX_2HX_{26}DX_2RX_3I$ (SEQ ID NO:14). In another embodiment, at least one purified protein has an amino acid sequence with at least 95% sequence homology with SEQ ID NO: 7. In another embodiment, at least one purified protein has an amino acid sequence comprising at least 95% sequence homology with an enzyme selected from PvuRts1I, PpeHI, EsaSS310P, EsaRBORFBP, PatTI, YkrI, EsaNI, SpeAI, BbiDI, PfrCORF1I80P, PcoORF314P, BmeDI, AbaSDFI, AbaCI, AbaAI, AbaSI, AbaUMB3ORFAP and Asp6ORFAP. In another embodiment, at least one of the purified proteins is selected from the group consisting of: PvuRts1I, PpeHI, EsaSS310P, EsaRBORFBP, PatTI, YkrI, EsaNI, SpeAI, BbiDI, PfrCORF1I80P, PcoORF314P, BmeDI, AbaSDFI, AbaCI, AbaAI, AbaSI, AbaUMB3ORFAP and Asp6ORFAP and catalytically active mutants and derivatives thereof.

In an embodiment of the invention, the buffer in the preparation may comprise a salt having an anion selected from a sulfate, a phosphate, an acetate or a citrate. In another embodiment, the buffer does not include a chloride, nitrate, carbonate or imidazole salt. The salt concentration may be in the range of 50-500 mM.

In an embodiment of the invention, a method is provided for detecting an hmC in a genomic DNA sample. The method includes adding a preparation as described above to the genomic DNA sample; permitting the protein to cleave the genomic DNA at a cleavage site; determining the DNA sequence at least on one side of the cleavage site; optionally mapping the DNA sequence onto a reference genomic DNA sequence; and detecting the hmC. The preparation used in the method may comprise: one or more of a DNA polymerase, primers and adapters.

In a further embodiment, the method includes amplifying the cleaved genomic DNA prior to determining the DNA sequence. In the above embodiments of the method, the genomic DNA may first be reacted with a β-glucosyl transferase (BGT) or labeled BGT or a derivative BGT prior to mixing the genomic DNA with the above defined preparation in a reaction vessel. In an embodiment, the method may be performed in a single reaction vessel or microfluidic device.

In an additional embodiment of the invention, a method is provided for purifying a ZZYZ family protein that includes: cloning and expressing a fusion protein comprising the ZZYZ family protein, an intein and an affinity-binding protein exemplified by a chitin-binding domain (CBD), a maltose-binding domain (MBP) or any other suitable protein capable of binding to a matrix; causing the fusion protein to bind to the matrix by means of the affinity-binding protein; cleaving the ZZYZ family protein from the intein; and recovering the purified protein in the eluate. In one embodiment, the affinity-binding protein is chitin-binding domain.

In an embodiment of the invention, a set of fragments is provided that includes at least one of (a) oligonucleotide fragments having a size of 20-23 nucleotides with a centrally positioned hmC or ghmC; or (b) large DNA or oligonucleotide fragments having an hmC or ghmC positioned on a single strand of a duplex DNA at a location of 11-13 nucleotides from the 3' end of the strand.

In an embodiment of the invention, a kit is provided that includes: one or more purified recombinant proteins of the ZZYZ family of proteins, functional derivatives thereof or catalytic fragments thereof in an effective buffer for permitting enzyme activity; and instructions for use. The kit may further include a BGT and UDP-glucose. The kit may further include primers. The kit may further include adapters suitable for use in sequencing platforms.

BRIEF DESCRIPTION OF THE DRAWINGS

FIG. 2 shows the sequence of a DNA substrate (SEQ ID NO:1) used in FIGS. 3-5. The substrate was prepared by PCR amplification such that each cytosine was either unmodified or replaced throughout by mC, hmC or ghmC. The mCs and hmCs were introduced into the substrate during PCR while the ghmC was the product of a glucosyl transferase reaction with the hmCs in the substrate. The primer sequence within the fragment did not contain a cytosine. An internal MfeI site was engineered into the PCR sequence in order to check the glucosylation status.

FIG. 3 shows the results for PvuRts1I where the ratio of hmC:ghmC:mC:C=2000:2000:8:1. The amount of the enzyme in the first lane adjacent to the left-side marker is 33 μg.

FIG. 4 shows the results for PpeHI where the ratio of hmC:ghmC:mC:C=128:256:2:1. The amount of the enzyme in the first lane adjacent to the left-side marker is 123 μg.

FIG. 5 shows the results for AbaSDFI where the ratio of hmC:ghmC:mC:C=500:8000:1:ND (not detected). The amount of the enzyme in the first lane adjacent to the left-side marker is 52 μg.

FIG. 6A shows the activity of purified recombinant PpeHI on a 56-base pair synthetic oligonucleotide substrate containing AhmCGT. Lane 1: DNA only, lanes 2-8: 2-fold dilution of the enzyme. The reactions were incubated at 37° C. for 1 hour and resolved on a 20% TBE polyacrylamide gel.

FIG. 6B shows a schematic digestion pattern of the oligonucleotide substrate showing products of cleavage. PpeHI cleaves on either side of the recognition site (shown by arrows) to create a 20-base pair fragment.

FIG. 8A shows the product of cleavage on the strand of the duplex complementary to the strand containing hmC corresponding to lanes 3 and 4 on the gel. The sequences of the oligonucleotides used are shown adjacent to the gel. The gel is the same as shown in FIG. 7. The synthetic oligonucleotide markers (M1, M5 and M2, M3) provide a guide to determine the cleavage sites. The oligonucleotide substrates and the synthetic markers were labeled with the fluorescent group FAM and resolved on a denaturing 20% polyacrylamide gel with 7M urea. The cleavage fragments corresponding to M2 and M3 (lane 3) and M1 and M5 (lane 4) are marked on the oligonucleotide sequence (SEQ ID NO:2) next to the gel.

FIG. 8B shows the product of cleavage on the strand of the duplex containing a ghmC. The substrate (R2) having the sequences (SEQ ID NOS: 3 and 4) shown was labeled with alpha-$^{33}$P dATP at each end (*). The markers (M1 and M2) are labeled with gamma-$^{33}$P ATP using polynucleotide kinase.

FIG. 8C shows that a ZZYZ protein cleaves DNA containing ghmC or hmC at the same distance 3' of the modified nucleotide. The glucosylation does not affect the cleavage distance. Different sets of substrates were used in the reaction, either with an hmC (lanes 1 and 3), or with a ghmC (lanes 2 and 4). Fluorescent labels (FAM) are indicated as filled circles in the Figure. Expected cleavage sites are marked with lines. The enzyme used here was AbaSDFI. By comparing lanes 3 and 4, it can be concluded that the cleavage distances on the opposite strand of the two types of modifications are same.

FIG. 13 shows a Promals (Pei & Grishin *Bioinformatics* 23(7):802-808 (2007)) alignment of members of a novel family of enzymes identified here as the ZZYZ family (SEQ ID NOS: 5-13). Nine members of the family are shown where each enzyme has preferential cleavage activity for hmC or ghmC compared with mC or unmodified cytosine in a double-stranded DNA (dsDNA).

DETAILED DESCRIPTION OF THE EMBODIMENTS

Figure 1:
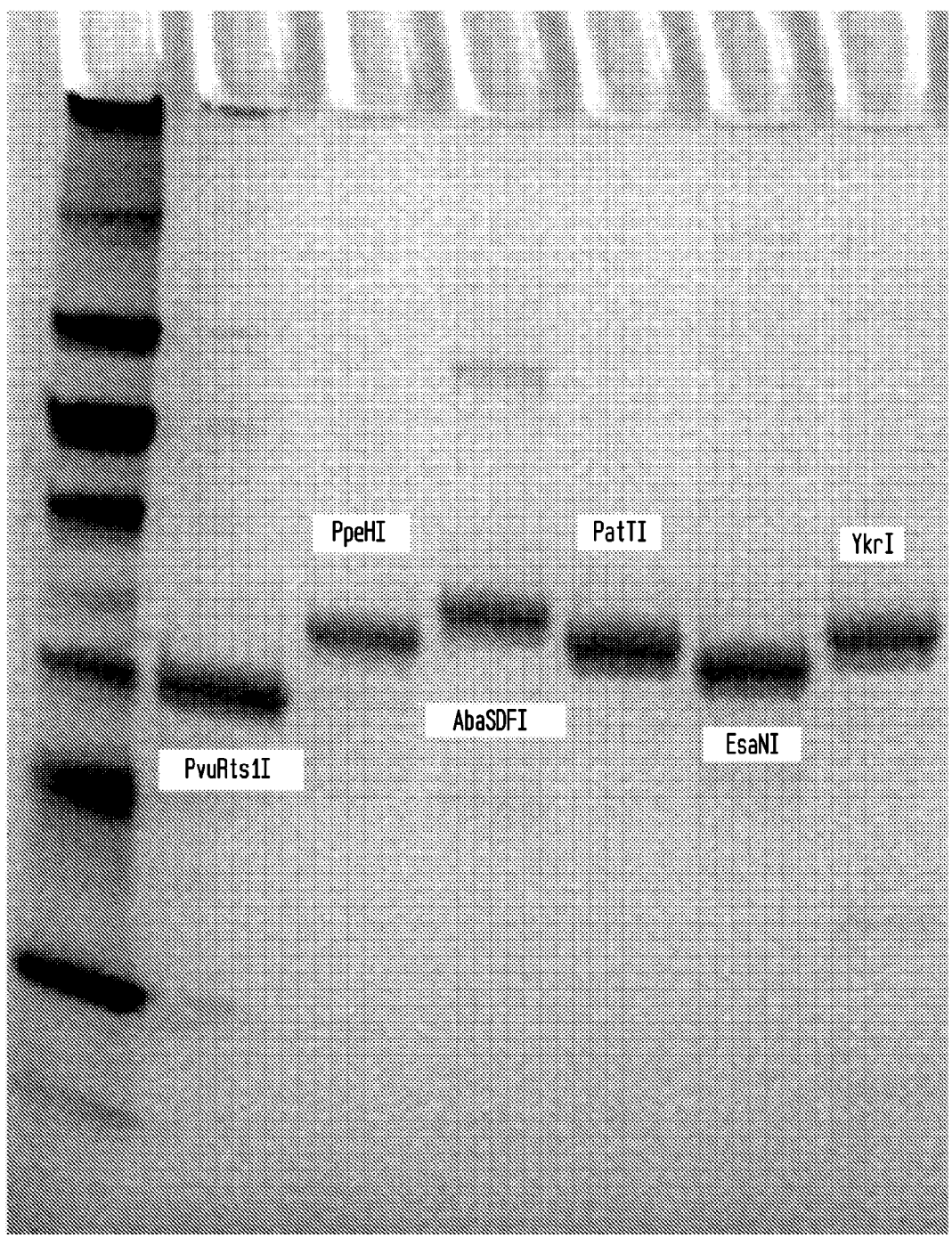
FIG. 1 shows the product of purification of representative enzymes from the ZZYZ family on a 10-20% denaturing polyacrylamide gel. Lane 1 is a size marker. Lane 2 is PvuRts1I, lane 3 PpeHI, lane 4 AbaSDFI, lane 5 PatTI, lane 6 EsaNI and lane 7 YkrI.

A unique feature of the family of enzymes described herein is its binding properties and cleavage specificity, which provide for the first time a direct enzymatic method to detect hmC in a genome including at hemi-hydroxymethylated sites quantitatively and in sequence context.

The newly defined ZZYZ family of enzymes described herein is of particular interest for reasons that include its ability to distinguish hmC (also ghmC) residues from mCs or unmethylated cytosines to produce a set of DNA fragments where cleavage occurs at a substantially fixed distance downstream of the enzyme recognition site on the DNA. The size of member fragments in a set of fragments resulting from cleavage with ZZYZ enzymes may be quite heterogeneous. When DNA has a hemi-hmC or hemi-ghmC, double-strand breaks occur on only one side (3') of the modified nucleotide to generate dsDNA fragments of variable length. dsDNA fragments will be generated of a size of 20-23 nucleotides when hmC or ghmC are symmetrically located in CpG sites.

Certain terms have been described below.

"Large DNA" is intended to refer to any naturally occurring or synthetic DNA having a size greater than 100 nucleotides up to a size of a genome.

"Similar size" with reference to a "set" of fragments is intended to refer to fragments that vary no more than about ±5 nucleotides in length.

"Centrally positioned" is intended to correspond to a location of a modified nucleotide on one strand which is approximately centered in the same strand of a dsDNA fragment. The location is generally within 5 nucleotides of the center determined by counting the nucleotides from either end of the fragment.

"N-terminal domain" refers to a region extending to about 50% of the amino acid sequence of the protein. "C-terminal domain" refers to a region extending to about 50% of the amino acid sequence of the protein.

A "matrix" is intended to include any structure having a surface suitable for immobilizing a molecule which has an affinity to the matrix and includes for example, beads, columns, flat surfaces such as paper or glass, the inside surface of a whole or hollow shape, etc.

A "set of fragments" is obtained by cleavage of a large dsDNA with an enzyme member of the ZZYZ family. The set of fragments include double-stranded oligonucleotides that are the product of cleavage of large DNA on both sides of symmetric hmCs or ghmCs (hmCG/GhmC) and fragments of variable size in which a hemi-hmC or ghmC is located at a fixed position from the cleavage site (e.g., 9-13 nucleotides). If a genome that consists of multiple large DNAs (e.g., chromosomes) is cleaved, each large DNA will give rise to a set of fragments. A mixture of fragments obtained from cleavage of an entire human genome can be considered as a plurality of sets of fragments, each set derived from a chromosome or as a single set of fragments depending on the context. In an embodiment, the set of fragments comprises at least 6 oligonucleotide fragments with different DNA sequences. For example, the set of oligonucleotides may comprise at least 10 fragments with different sequences or at least 20 fragments with different sequences. In one embodiment, the set of oligonucleotides includes one or more similarly sized fragments with a centrally located hmC or ghmC.

An "enzyme preparation" is intended to refer to a reagent and not something occurring in its natural state in vivo.

"X" when used in an amino acid sequence represents any amino acid.

A novel family of DNA cleavage enzymes is identified here as the ZZYZ family where the members of the family preferentially recognize an hmC and ghmC and not methylated (mC) or unmodified cytosines in dsDNA and then cleave DNA at a non-random distance downstream (3' direction) from the hmC or ghmC nucleotide on each DNA strand that contains the hmC or ghmc. Members of this family include but are not limited to bacterial restriction endonucleases.

Members of the family may be characterized structurally by a distinct cleavage domain and a binding domain and in particular by an N-terminal conserved domain with greater than 85% amino acid sequence homology, for example greater than 90% amino acid sequence homology for example greater than 98% sequence homology with $RX_7KX_2EXYX_{18}QQX_{11-16}DLX_2PX_6EXDEX_2HX_{6-26}DX_2RX_3I$ (SEQ ID NO:14) in the N-terminal domain, and/or greater than 85% or 90% or 98% amino acid sequence homology with $WXNX_{30-40}AX_{12-13}FXGX_{16-18}R$ (SEQ ID NO:15) in the C-terminal domain. In one embodiment, a protein (exemplified by AbaSDFI) with an N-terminal sequence of $RX_7KX_2EXYX_{18}QQX_{11-16}DLX_2PX_6EXDEX_2HX_{26}DX_2RX_3I$ (SEQ ID NO:16) had a high degree of selectivity between ghmC/hmC and mC.

Members of ZZYZ family (see for example FIG. 13) include recombinant proteins, variants and derivatives. Examples of variants include mutants, in which for example the catalytic domain has been modified or removed from the protein and only the DNA binding domain for hmC and ghmC remains. Additional examples of variants are fusion proteins. These fusion proteins may serve as reagents or may be intermediates in the purification of the enzymes or the mapping of the hydroxymethylated nucleotides.

Fusion protein variants in the ZZYZ protein family may be fused to a second protein or a plurality of proteins that serve as a label, tag or marker for visualizing in situ the protein bound to hmC or ghmC or for affinity purification. Examples of fusion partners include inteins (U.S. Pat. No. 5,643,758), maltose-binding proteins (MBPs) (U.S. Pat. Nos. 5,643,758 and 7,825,218; and PCT Publication No. WO 2010/114532), SNAP-TAG® (U.S. Publication No. US-2004-0115130) or may contain a substitution which acts as a label for example, substituting a cysteine for a selenocysteine (see U.S. Pat. No. 7,141,366). Alternatively, the fusion protein may include a nucleic acid aptamer for tagging or purification (see for example, U.S. Pat. Nos. 5,670,637; 5,696,249; 5,874,557; 5,693,502).

Members of the family share with each other at least 30% amino acid sequence identity for example at least 40% for example at least 50% for example at least 50% for example at least 60% for example at least 70% for example at least 80% for example at least 90% or at least 95% amino acid sequence similarity as defined by a Promals alignment (Pei & Grishin *Bioinformatics* 23(7):802-808 (2007)) and include PvuRts1I, PpeHI, AbaSDFI, EsaSS310P, EsaRBORFBP, PatTI, YkrI, EsaNI, SpeAI, BbiDI, PfrCORF1I80P, PcoORF314P, and BmeD1 some of which are described in Table 1 and in FIG. 13. For example, one family member is AbaSDF1 where variants AbaCI (GenBank:ACQB1000053), AbaAI (GenBank: ABXK01000045), AbaSI (GenBank: NC_009085), AbaUMB3ORFAP (GenBank:AEPM01000006) and Asp6ORFAP (GenBank: ACYS01000207 share at least 95% sequence similarity with AbaSDF1. These enzymes are not included in Table 1. Their properties are substantially the same as AbaSDFI. Reference to the individual members of the family are intended to include derivatives and catalytically active fragments thereof.

Antibodies may be raised to members of the ZZYZ enzyme family using standard techniques for generating monoclonal or polyclonal antibodies or antibody fragments. These antibodies or fragments thereof may be used for in situ-labeling of a member of the ZZYZ enzyme family bound to the hydroxymethylated or glucosylated hydroxymethylated large DNA.

One member of the ZZYZ family of enzymes is PvuRts1I. This restriction endonuclease was first described by Ishaq & Kaji (*Biological Chemistry* 255(9):4040-4047 (1980)) and shown to be a hmC-specific restriction endonuclease that is encoded by the plasmid Rts1. The PvuRts1I gene was cloned and expressed (Janosi and Kaji, FASEB J. 6: A216 (1992); Janosi et al. *Journal of Molecular Biology* 242: 45-61 (1994)) and the Rts1 plasmid was completely sequenced (Murata et al. *Journal of Bacteriology* 184(12):3194-202 (2002)).

However, no in-depth study of this enzyme has been carried out or published. Furthermore, after the initial publications, there has been little interest in this enzyme. This was highlighted by PCT Publication No. WO 2010/037001 which has a section on detection methods for hmC and ghmC, but omits any mention of this enzyme. WO 2010/037001 describes methods that are chemical in nature or involve binding proteins such as antibodies. Where enzymes are referred to, these are exemplified exclusively by glucosyl transferases.

In order to study the properties of this family such as specificity, it was necessary to purify the enzymes. After careful analysis and extensive experimentation, it was discovered that many commonly used ionic reagents in purification, such as NaCl, inactivated the enzymes. It was further discovered that the use of different types of salts and their concentrations affected activity. It was found that the ZZYZ family of enzymes was inactivated in the presence of salts such as chlorides, nitrates, carbonates or imidazole salts. Therefore, it was concluded that these salts should be avoided. Other salts such as sulfates, phosphates, acetates and citrates appeared to inhibit enzyme activity at high concentrations and therefore it was preferable to store or use enzymes at concentrations in the range of about 50-500 mM.

Another important consideration was the discriminatory properties of the enzyme for hmC over mC and C. Since hmC is predicted to occur very infrequently in the genome, low levels of cleavage at mC or C could result in a high background that would affect the ability to detect hmC.

Purification of the ZZYZ family members would permit a study of the cleavage properties of the enzyme family. Initial attempts to purify native or recombinant PvuRts1I was problematic, since all standard columns commonly used for purification led to significant loss of enzyme activity. Recombinant PvuRts1I was made as a fusion protein with 6xHis-tag positioned on its C-terminus or N-terminus. 6xHis-tag on the N-terminus of PvuRts1I had the undesirable effect of greatly increasing the cleavage activity of the enzyme on the unmodified substrate, thus reducing the utility of the enzyme to detect hmC directly. The C-terminal addition of a 6xHis tag did not change the relative activity on each substrate of different methylation status, but the specific activity of the enzyme was lowered significantly.

Recombinant PvuRts1I was also fused to an intein-CBD (IMPACT™ kit, NEB) which was then cleaved to release purified enzyme. High yields of active enzyme could be obtained this way (see Example 1).

The recombinant protein either alone, modified or fused to a tag may be labeled for imaging purposes using a spectroscopic label such as a fluorescent or chemiluminescent label, a radioactive label, or other reactive chemical agent, or a labeled sugar, a labeled antibody or other labeled protein tag, (including for example SNAP-TAG®, NEB) (also see Chun-Xiao Song et al. *Nature Biotechnology* 29: 68-72 (2011)).

Figure 3:
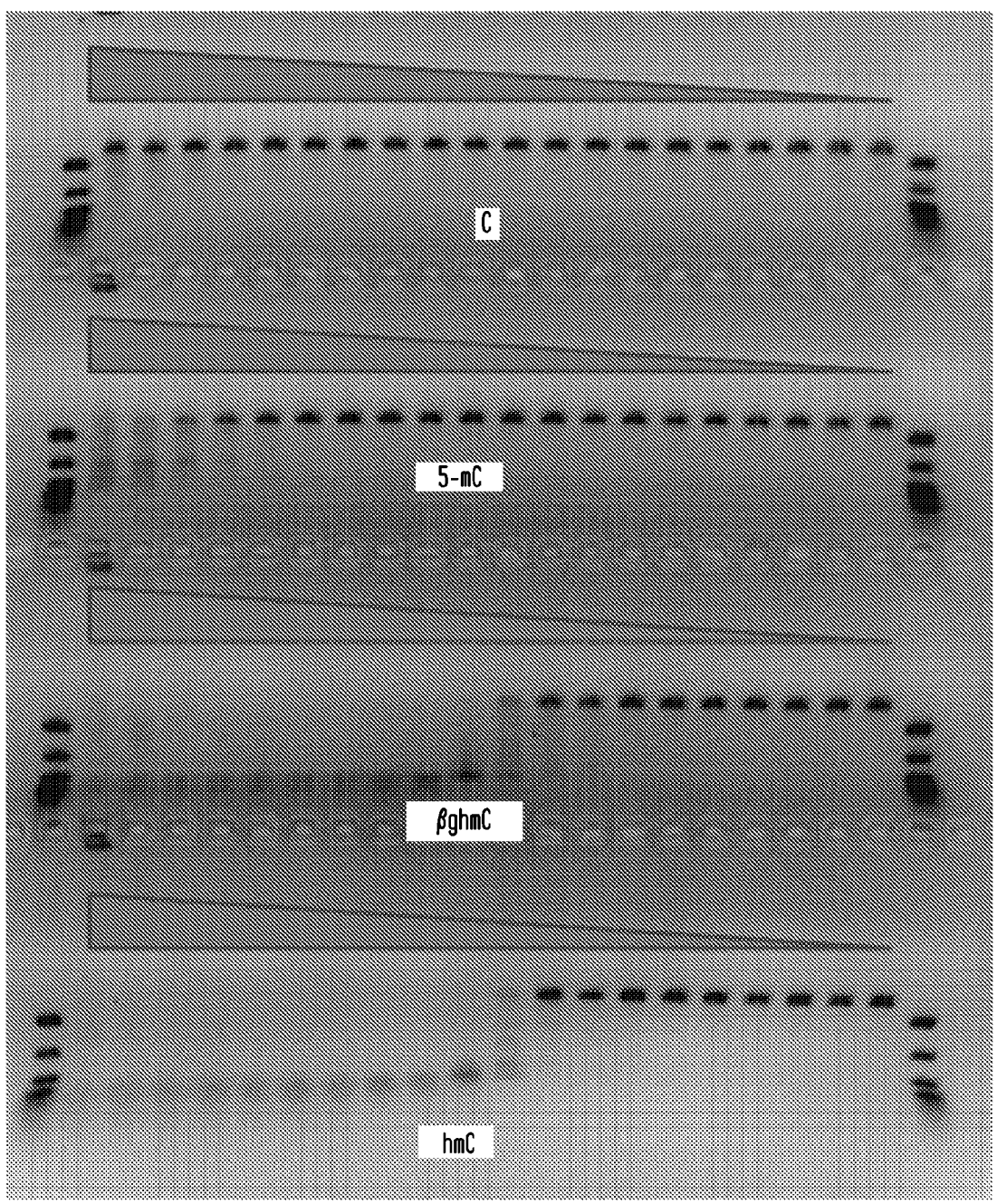
FIGS. 3-5 show the product of the reaction between 2-fold serial dilutions of representative enzymes in the ZZYZ family and the substrate from FIG. 2 in which all the Cs are unmodified, all the Cs replaced by mCs, all the Cs replaced by ghmCs (βghmCs) and all the Cs replaced by hmCs. The first and last lanes contain the PCR marker. The lanes in between the markers show two-fold serial dilutions of a single enzyme. The reaction conditions were 23° C., 20 min in NEB4 buffer (New England Biolabs, Inc., Ipswich, Mass. (NEB)) with the final KOAc concentration at 250 mM.
Figure 4:
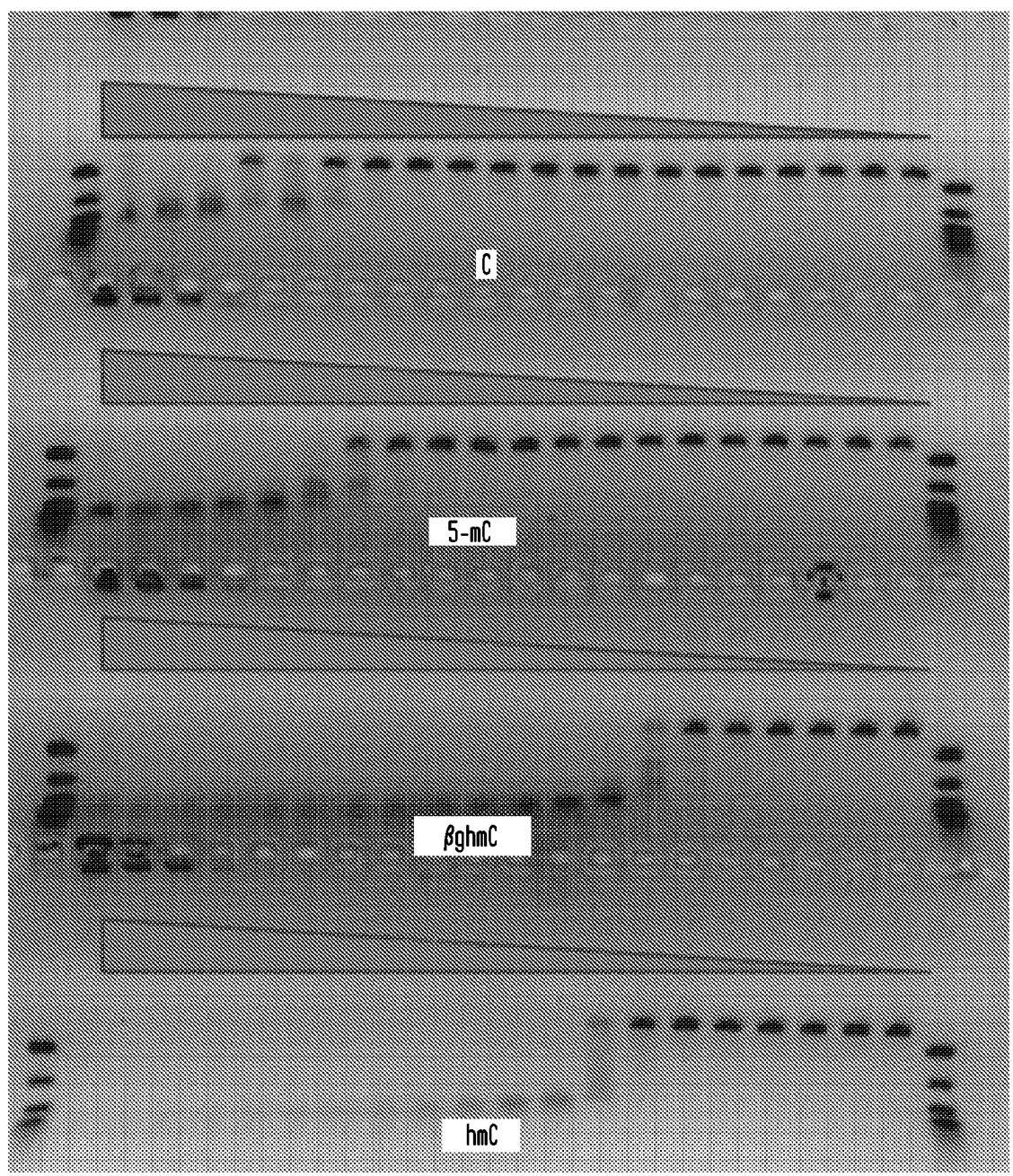
Figure 5:
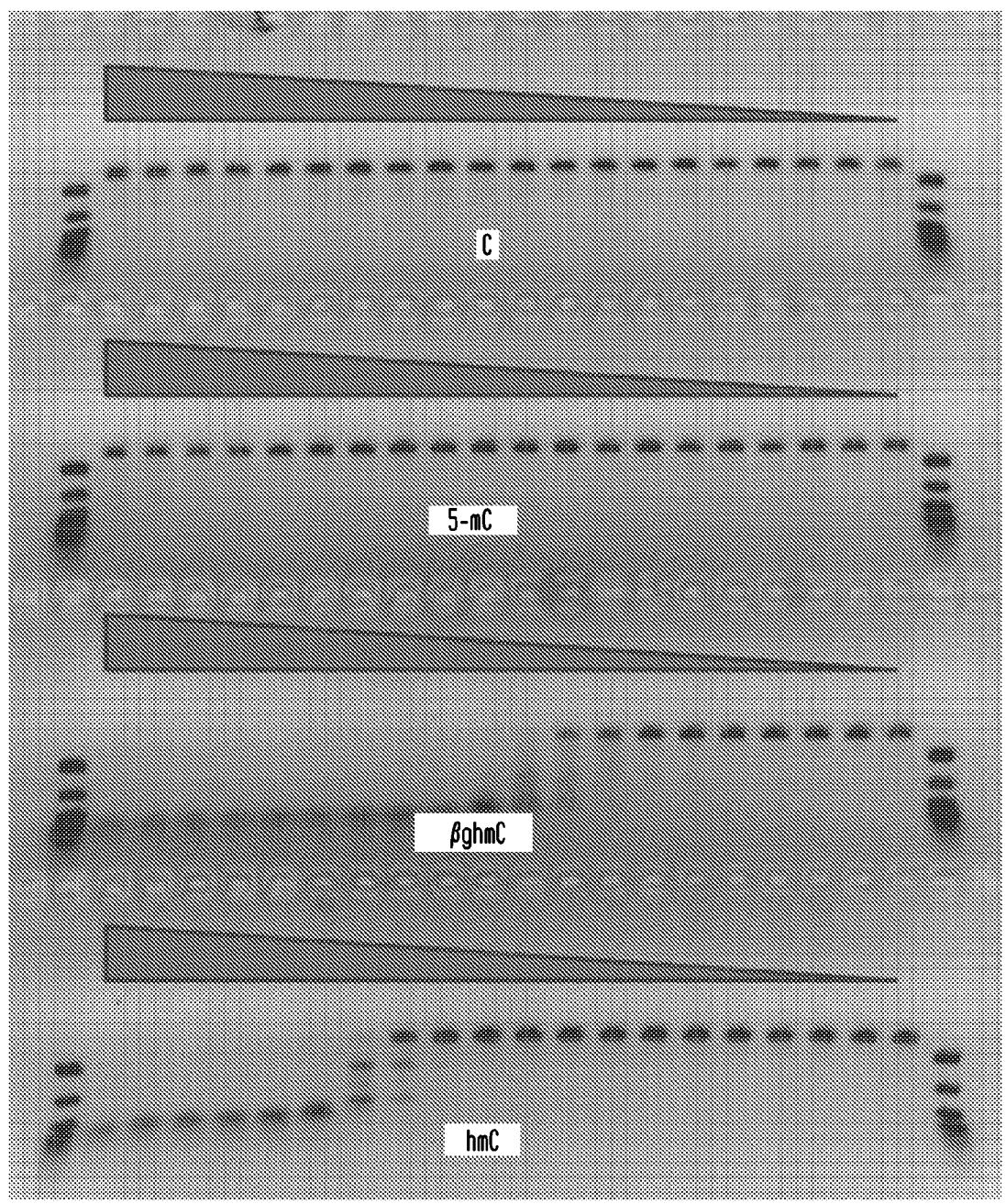

The application of the assay, shown in FIGS. 3-5 to determine concentrations of enzyme at which maximal ghmC- and hmC-specific cleavage occurred and minimal mC and C cleavage was detected, enabled the identification of the cleavage properties of ZZYZ family members. The results obtained from this analysis of specificity (for example see Table 1) showed that members of this family offered a significant improved and simplified method for specifically identifying and mapping hmC in DNA.

A feature of the reagents for effective analysis of hmC in a genome includes the discriminatory power of the reagents for hmC and/or ghmC over mC and C. Hence, ratios were determined for enzyme cleavage specificity. Examples of ratios for different enzymes in the ZZYZ family are provided in Table 1.

The purified enzymes in the ZZYZ family were found to have a minimum ratio of cleavage for hmC or ghmC:mC of at least 8:1 for example, 50:1, for example at least 100:1, for example at least 200:1 or for example at least 250:1; and a minimum cleavage ratio of hmC or ghmC:C of at least 50:1, for example at least 100:1, for example at least 200:1 or for example at least 250:1. These ratios can be determined according to the assay described in Example 1 and FIGS. 3-5.

To improve the consistency of the assay, PCR DNAs were used as a substrate in place of phage T4 and lambda DNA. hmC-, mC- and C-containing DNA substrates were obtained by PCR of a synthetic oligonucleotide obtained commercially (Integrated DNA Technologies (IDT), Coralville, Iowa) in which hydroxymethylated deoxycytidine triphosphate (hmdCTP) or methylated deoxycytidine triphosphate (mdCTP) were substituted for dCTP as desired. The hmC PCR fragment was further glucosylated by BGT to become a ghmC PCR DNA fragment. The results of this assay showed for example that PvuRts1I has an activity ratio of hmC:ghmC:5-mC:C=2000:2000:8:1; for PpeHI, it is 120:250:2:1; for AbaSDFI, it is 500:8000:1:ND. ND indicates there is no observable cleavage even at the highest concentrations of enzyme.

Figure 6B:
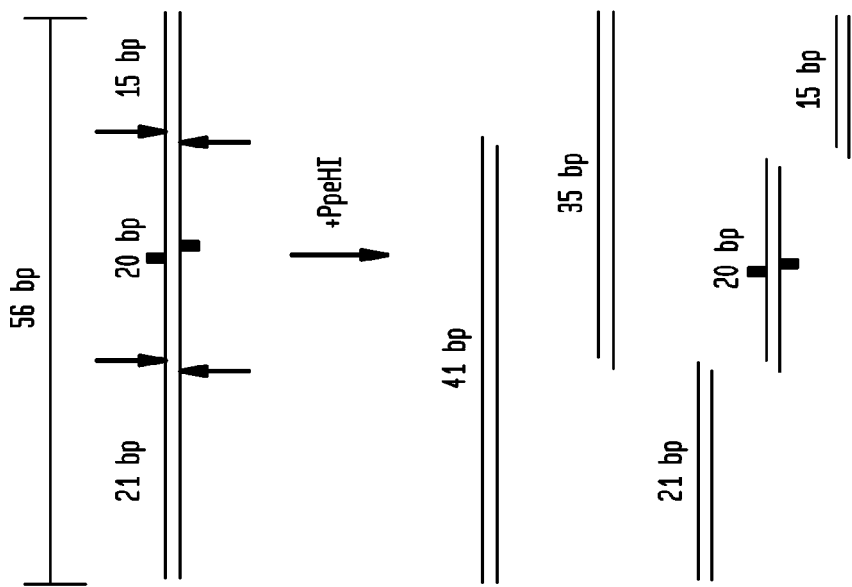
FIGS. 6A and 6B show that the ZZYZ family of enzymes cleaves fully hydroxymethylated oligo substrates.
Figure 6A:
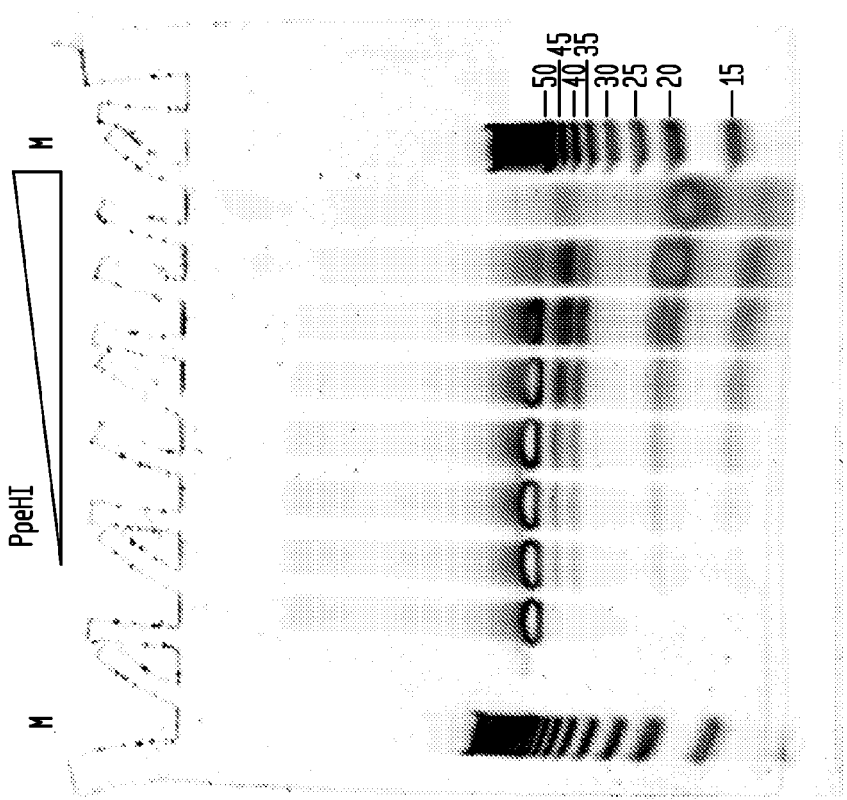

A feature of the ZZYZ family members is that the precise cleavage site 3' downstream of the hmC or ghmc may vary by no more than 5 nucleotides, for example, not more than 3 nucleotides. For example, it was shown using synthetic substrates (see for example, Example 3 and FIGS. 6-8) that although members of the ZZYZ family predominantly cleaved dsDNA at a single defined distance from the hmC or ghmC, the cleavage site could occur at 11-13 nucleotides distant from the hmC or ghmC on one strand and 9-10 nucleotides distant from the hmC or ghmC on the opposite strand (ghmCN$_{11-13}$/N$_{9-10}$). A cleavage fragment of about 20-23 bp results from cleavage at a symmetrical hmC site (hmCG/GhmC) on a duplex DNA.

An appreciation of the variation in the cleavage distance by the ZZYZ family of enzymes is important for mapping the location of hmC bases in a genome. It was also established in FIG. 8C that the presence of a ghmC in place of hmC had no observable effect on the cleavage distance. It was noted, however, that cleavage activity may be enhanced if a G is located at 21-22 nucleotides from the ZZYZ recognition site on the opposite strand although there is no absolute requirement for a G at that location nor is there any significant or even detectable nucleotide bias immediately flanking ghmC or hmC.

Figure 9:
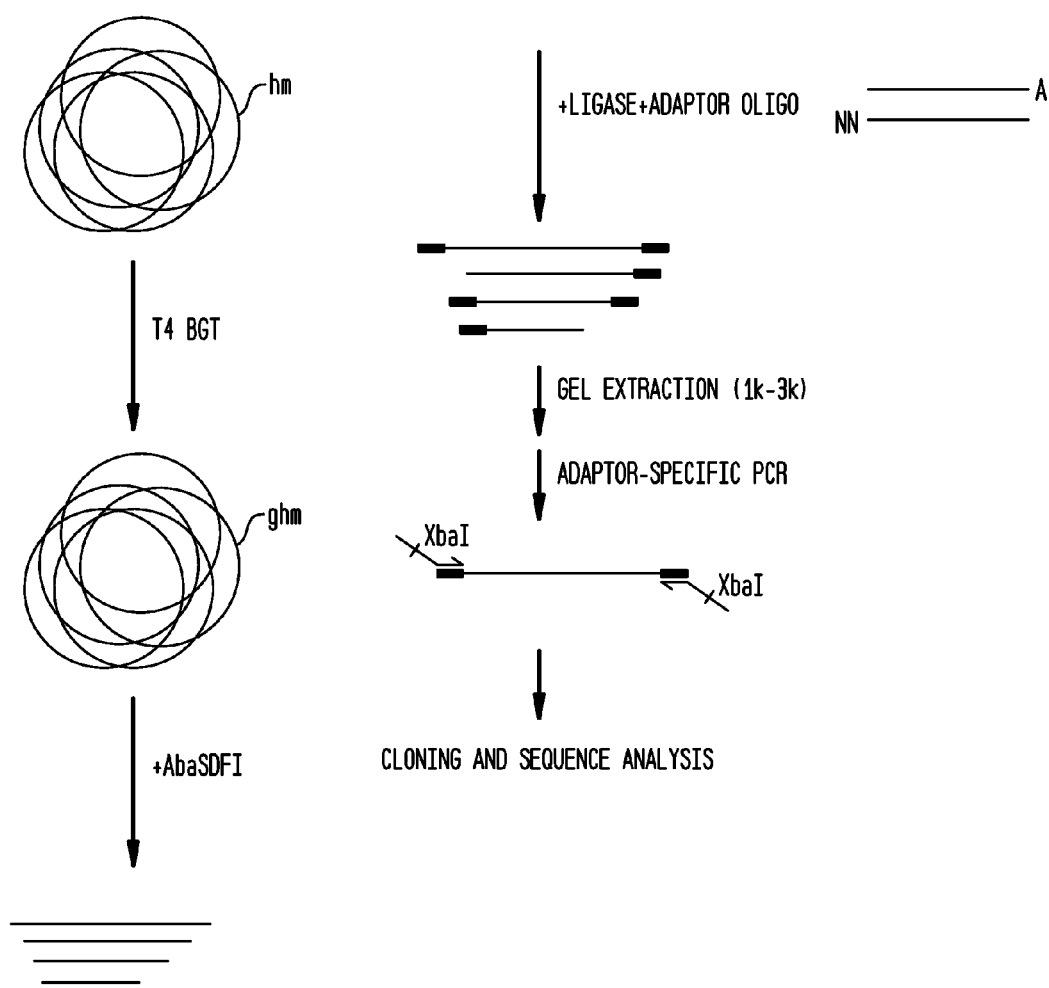
FIG. 9 shows a method for identifying hmC sites in rat brain genomic DNA. Genomic DNA was treated with T4 BGT to glucosylate any hmCs and then digested with a ZZYZ enzyme (e.g., AbaSDFI). The digested products were ligated with a synthetic double-stranded oligonucleotide adaptor, as illustrated. The ligatable end had the 2-bp degenerate nucleotides. Ligated fragments were size-selected from approximately 1 kb-3 kb. These were PCR-amplified using the common primer specific to the adaptor. The amplified PCR products can then be cloned into a common cloning vector and sequenced to determine which of the adjacent cytosines is hydroxymethylated.

The location of hmC or ghmC in a large DNA can thus be deduced by cloning the cleavage products and/or by sequencing, for example, ultra high throughput sequencing platforms (see Example 7). Using ZZYZ family members, it is possible to identify and map hmCs or ghmCs and differentiate these from mCs in a single enzyme reaction. Where two hemimethylated CpG sites are close together, it is possible to determine which of the 4 possible positions contains the hmC (for example, FIGS. 9-11).

The use of the ZZYZ family of enzymes to generate a set of fragments for genomic analysis of hydroxymethylation or other purpose may rely on a single enzyme or may include a plurality of enzymes where some or all of the enzymes are: members of the ZZYZ family; derived from members of the ZZYZ family; include members of the MspJI family (PCT Publication No. WO2010/075375) of enzymes and/or the MmeI-like family of restriction endonucleases; and/or other types of restriction endonucleases.

One of the features that characterize the ZZYZ family of proteins is the presence of a binding domain (C-terminal) and a catalytic domain (N-terminal). The binding domain of ZZYZ-like enzymes can be utilized for both in vivo and in vitro applications. Examples of uses of the binding domain include: in vitro enrichment of hmC-containing DNA for example as a reagent for affinity purification or in vivo targeting of hmC. The latter may be achieved by labeling the binding domain or fusing the binding domain with other domains to bring them to the hmC sites in the genome. The binding domain may also be fused with a nuclease domain to trigger double-stranded breaks in the vicinity of the hmC sites to activate DNA repair pathway, so that the epigenetic status of those sites can be changed.

Determining the level of hydroxymethylation of DNA samples is important for epigenetic studies. Epigenetic regulation of the genome includes chromatin-remodeling which relies in part on converting mC to hmC. Differences in hydroxymethylation patterns may be critical indicators of inappropriate developmental processes for example for embryonic stem cells. These differences can now be studied in a convenient manner using an enzyme from the ZZYZ protein family which selectively targets hmC and ghmC. These nucleotide modifications can then be mapped onto a methylome or genome.

PCT Application No. PCT/US2010/046632, incorporated in its entirety herein, further elaborates on the significance of mapping hydroxymethylated nucleotides in the genome for understanding the phenotype of a host cell and an organism. The ZZYZ family alone or in conjunction with other enzymes (for example, a member of the MspJI family or MspI or enzymes functionally related to MspI) may be used to provide a methylome and hydroxymethylome simultaneously using a sequencing technique described herein or other sequencing techniques known in the art.

The set(s) of fragments, resulting from enzyme cleavage with one or more enzymes from the ZZYZ family and optionally other DNA cleavage enzymes that cleave modified nucleotides, can be sequenced using high throughput sequencing methods of the sort that are currently available using for example NextGen sequencing methods to identify and map hmCs or ghmCs in DNA. Selection of specific cleavage products that hybridize to particular regions of the genome may be used for rapid diagnostic methods to reveal the abnormal presence or absence of hmCs or ghmCs correlated with a disease such as cancer. Specific oligonucleotides may be used to determine a particular phenotype for an individual. For example, hybridization of a set of fragments to a defined sequence or set of sequences presented on a solid surface (array hybridization) or tagged in a solution (or visa versa) can reveal discrepancies between fragments in the set and a standard set of fragments that characterize the methylome. qPCR or array hybridization may also be used to interrogate one or more known locations of interest for abundance. The hmC or ghmC or binding domain may be labelled with a fluorescent or chemiluminescent tag or other labelling methods known in the art to facilitate detection.

The purification of members of the ZZYZ family of enzymes and the characterization of its cleavage specificities and its ability to discriminate hemi-hmC from symmetric hmC provide for the first time the type of data generation that is required in research, medical diagnostics and treatment to understand the role and implications of hydroxymethylated DNA for any particular phenotype.

The detailed descriptions of medical conditions are provided by PCT Publication No. WO2010/037001 which is herein incorporated by reference in its entirety. In every circumstance where TET proteins are involved in gene expression, it will be necessary to identify where the hmC that is created by TET is located, and thus it will be desirable to use the ZZYZ family described herein.

TABLE 1

Examples of members of the ZZYZ family of proteins

| Name | Alternative name | hmC | ghmC | mCG | C | Length, similarity and identity to PvuRts1I | Source |
|---|---|---|---|---|---|---|---|
| PvuRts1I | PvuRts1I | 2000 | 2000 | 8 | 1 | 293, 100%, 100% | *Proteus vulgaris* (Rts1) |

TABLE 1-continued

Examples of members of the ZZYZ family of proteins

| Name | Alternative name | hmC | ghmC | mCG | C | Length, similarity and identity to PvuRts1I | Source |
|---|---|---|---|---|---|---|---|
| PpeHI | PROPEN_01738 | 128 | 256 | 2 | 1 | 294, 72.5%, 64.6% | *Proteus penneri* ATCC 35198 |
| PatTI | Pat1_1499 | 2000 | 8000 | 128 | 1 | 306, 51.4%, 36.5% | *Pseudoalteromonas atlantica* T6c ATCC BAA-1087 |
| YkrI | Ykris0001_38440 | 250 | 1000 | 64 | 1 | 299, 49.6%, 36.1% | *Yersinia kristensenii* ATCC33638 |
| EsaNI | GOS_7810815 | 128 | 64 | 8 | 1 | 299, 47.8%, 39.6% | Marine metagenome |
| AbaSDFI | ABSDF3356 | 500 | 8000 | 1 | 0 | 317, 47.8%, 35.4% | *Acinetobacter baumannii* SDF |
| SpeAI | Spea_2956 | | | | | 285, 47.1%, 35.6% | *Shewanella pealeana* ATCC 700345 |
| BbiDI | BbifN4_02244 | | | | | 311, 43.3%, 32.0% | *Bifidobacterium bifidum* NCIMB 41171 |
| BmeDI | | | | | | 300, 40.0%, 30.5% | *Bacillus megaterium* strain DSM319 |

The experimental protocols provided are not intended to be limiting. One of ordinary skill in the art could employ the experimental design as provided below to any additional member of the newly defined family.

All references cited herein, including U.S. provisional application Nos. 61/376,932 filed Aug. 25, 2010 and 61/296,630 filed Jan. 20, 2010, are incorporated by reference.

EXAMPLES

Example 1

Purification of ZZYZ Proteins and Assay for Activity and Specificity

The selected sequences recognized by a BLAST search (Zhang et al. *J. Comput. Biol.* 7(1-2): 203-214 (2000)) and determined to be a member of the ZZYZ family may be expressed by techniques known in the art, for example in vitro transcription-translation (PURExpress®, NEB. The gene can be optionally codon-optimized and then cloned as described below for PvuRts1I.

PvuRts1I was purified as follows: A gene encoding PvuRts1I was inserted into a pTXB1 vector (NEB), cloned in ER2566 (a T7 expression host) and grown in LB with Ampicillin (100 µg/ml) at 30° C. for 4×10 ml overnight culture. 4×10 ml overnight cultures were inoculated into 2×1 L LB with Ampicillin (100 µg/ml). After the 1 L culture was grown at 30° C. for 6 hours, IPTG was added to the culture to a final concentration of 500 µM. The culture was further incubated at 16° C. overnight. The PvuRts1I was purified using a chitin-bead gravity column. After the PvuRts1I was loaded onto the column in a high salt buffer (10 mM Tris-Acetate, 500 mM KoAc, pH8.0), the column was washed again with the high salt buffer. Three column volumes of high salt buffer containing 30 mM DTT were used to flush the column thoroughly. The column was incubated for 16 hours at 4° C. in the high salt buffer with DTT. The protein was thus eluted and concentrated. A total of about 10 mg PvuRts1I was obtained. The protein was then added to 50% glycerol and stored in −20° C. for further gel characterization. When 1 µg of the eluant was run on a 10% to 20% polyacrymide gel, bands of purified enzyme were detected, confirming the purity of the enzymes (see FIG. 1). This method was also used to purify other members of the ZZYZ family such as PpeHI, AbaSDFI, PatTI, EsaNI and YkrI.

To assay the purified enzyme for substrate activity and specificity, a synthetic substrate as described in FIG. 2 was amplified using PCR. Cytosine, mC or hmC was used in the PCR reaction to produce a product with either unmodified C or fully modified C. The PCR product with hmC was subsequently reacted with BGT and UDP-glucose to convert hmC to ghmC.

The analysis of substrate specificity and activity was performed as follows: a reaction mixture was formed which contained the enzyme (3 µl containing 33-123 µg enzyme), 3 µl potassium acetate (final concentration of 250 mM) and NEB4 buffer (NEB), 50 ng of the DNA substrate in which cytosine is unsubstituted or substituted with hmC, ghmC or mC, and water added to a final reaction volume of 30 µl.

The enzyme was serially diluted and added to the reaction mixture which was incubated for 20 min at room temperature (23° C.) and then loaded onto a 1.8% agarose gel. The reaction was stopped by stop solution and results are shown in FIGS. 3-5 and summarized in Table 1. The range of cleavage in the Table 1 shows that hmC was recognized and cleaved at least 50-fold more actively than cytosine and greater than 8-fold more than mC. For AbaSDF1, the relative cleavage activity was 8000-fold more active for ghmC than for hmC and 500-fold more active for hmC than for mC and no activity for C was detected.

In addition to assaying for activity and relative specificity (ratios), the equilibrium dissociation constant ($K_d$) for ZZYZ family members can be determined. Accordingly, the rate of reaction of enzymes with different modified substrate oligonucleotides can be determined using gel mobility shift assays on Micropure-EZ columns (Millipore, Billerica, Mass.). For example, constant amounts of the labeled oligonucleotides can be mixed with increasing amounts of enzyme under non-cleaving conditions, e.g., without $Mg^{2+}$, and the enzyme-DNA mix analyzed on a native polyacrylamide gel, or using spin columns which only retain DNA oligonucleotides (cleavage products) when the enzyme is bound. The $K_d$ data can be used in soaking experiments to acquire co-crystals. In addition, the $K_d$ of the C-terminal domain which serves as a binding module for the hydroxymethylated base and its flanking sequences in the substrate can be similarly determined.

Example 2

Figure 7:
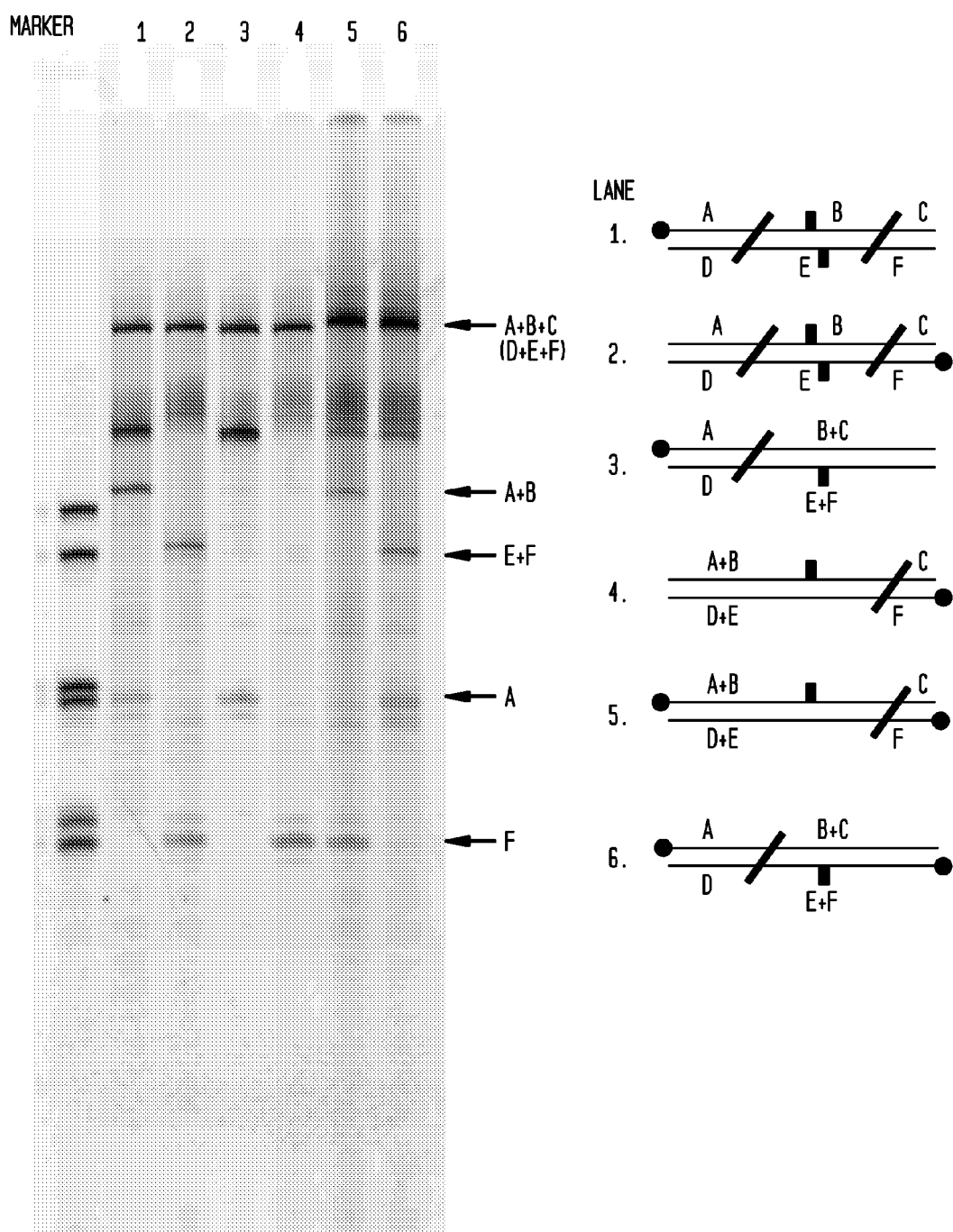
FIG. 7 shows the activity of ZZYZ enzymes on symmetrically hydroxymethylated oligonucleotides and hemi-hydroxymethylated oligonucleotides. The gel shows results using PpeHI. The digestion products were analyzed on a 20% polyacrylamide denaturing gel with 7M urea. The numbered lanes on the gel correspond to the cleavage patterns shown by cartoon on the right of the gel. For example, lane 1 corresponds to the cleavage pattern resulting from hmCG/GhmC on the top and bottom strand with the top strand only being labeled.

Determination of the Cleavage Location on Substrate by Members of the ZZYZ Family To confirm that the ZZYZ family of proteins cleaves dsDNA, 3' downstream of the recognition nucleotide at a fixed position, synthetic oligonucleotides were created which were labeled on one strand or both strands and which contained symmetrical hmC or ghmC nucleotides or were hemi-hydroxymethylated as shown in FIG. 7. All oligonucleotides with fluorescent labels were made using standard techniques of organic synthesis using hmC phosphoramidite (Glen Research, Sterling, Va.). dsDNAs were formed by allowing the two oligonucleotides to anneal to 10 μM solution. All digestions were carried out in NEB4 buffer (NEB). In each digestion, 10 pmol of substrate was incubated with 1 unit of PpeHI in 37° C. for 1 hour. One unit is defined as the amount of enzyme needed to digest 1 μg of T4gt DNA into stable pattern of small fragments in 37° C. for 1 hour. 2 μl of each reaction mixture was then loaded onto 20% polyacrylamide gel with 7M urea. The results are shown in FIG. 7. Arrows show bands corresponding to the cleavage fragments shown on the right of the gel. The results show that the enzyme is capable of cleaving on both sides of the recognition sequence at approximately substantially fixed distance from the recognition site.

Example 3

Determination of Cleavage Distance on Each Strand of Duplex DNA

Figure 8A:
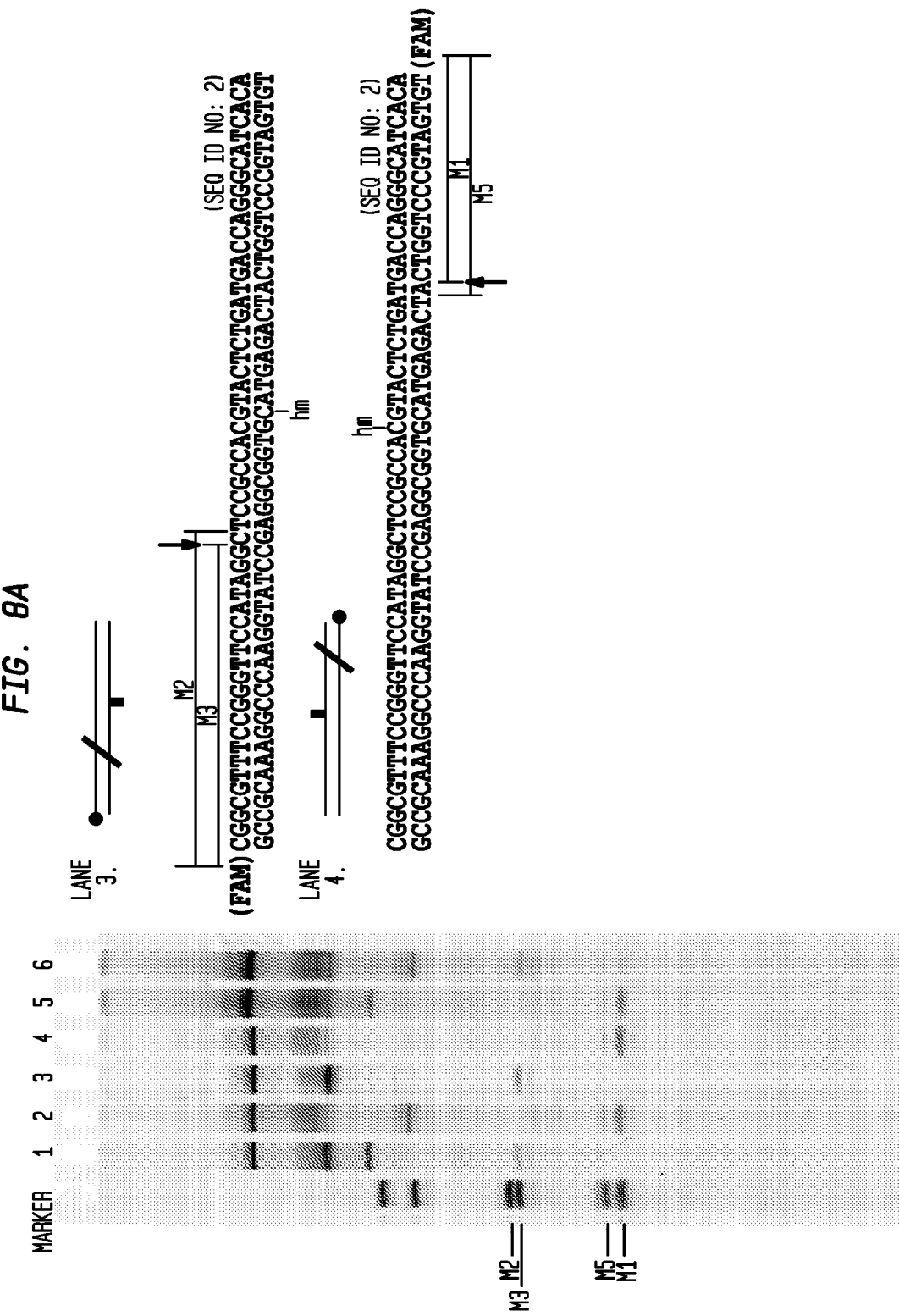
FIGS. 8A-B shows the cleavage sites of ZZYZ family enzymes as determined separately for each strand of a DNA duplex containing an hmC or ghmc on one strand.

The specificity of cleavage distance was also determined. Labeled and unlabelled oligonucleotides containing hmC were synthesized using standard organic synthesis techniques, as described in Example 2. Oligonucleotide size markers were also synthesized to determine the cleavage sites, as shown in FIG. 8A. Lanes 3 and 4 demonstrate that the cleavage sites in the complementary strand of the hmC-containing strand were 9-10 nt on the 3' side from the hmC.

Figure 8B:
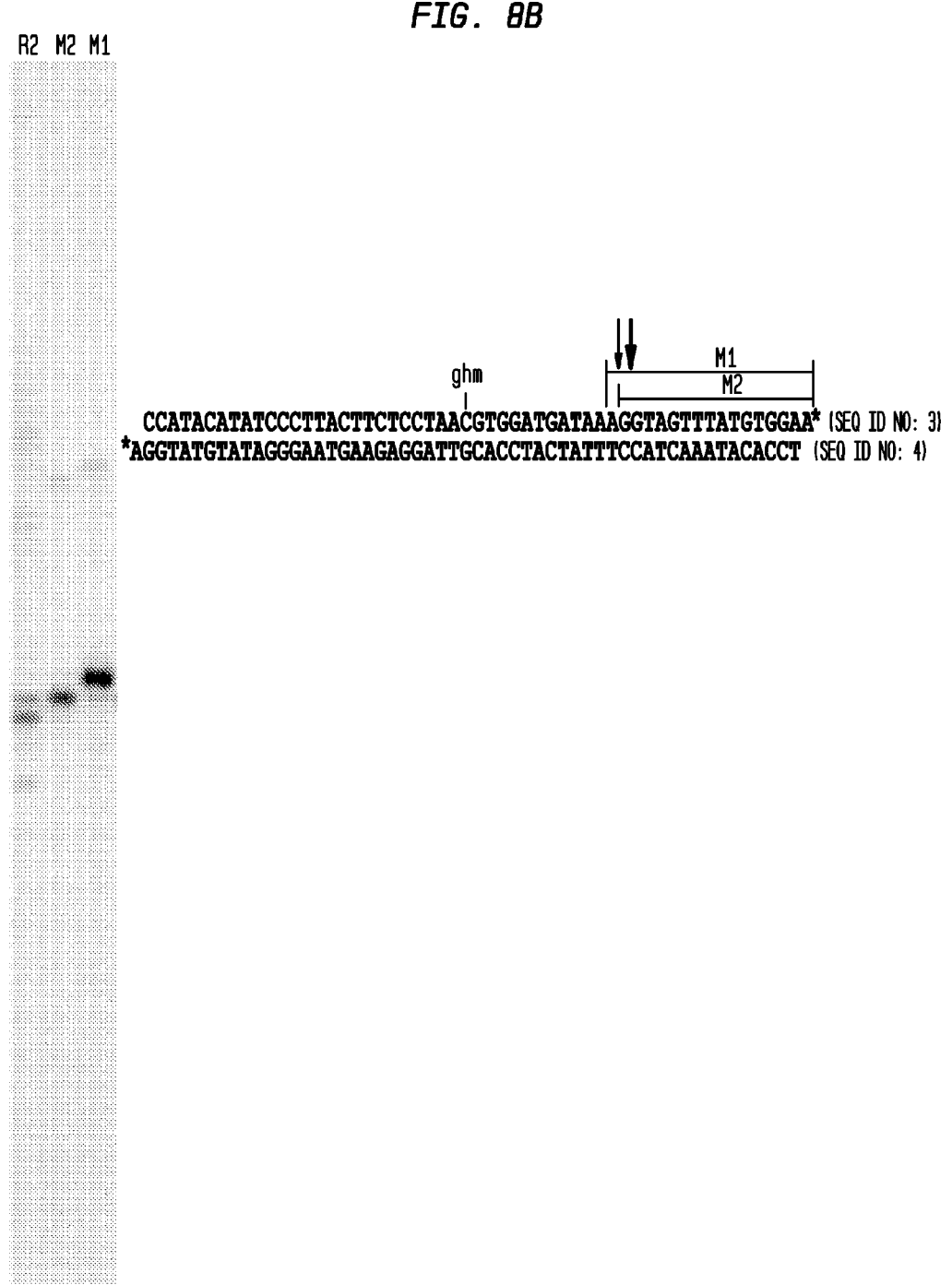

To determine the cleavage sites in the same strand of the hmC, dsDNAs were formed by allowing the oligonucleotides containing hmC to anneal to oligonucleotides containing unmodified cytosine in 20 μM solution. 40 μl of annealed DNA was treated with T4 BGT (NEB) according to the manufacturer's protocol. After the reaction, the DNA was purified through QIAquick® nucleotide removal kit (Quigen, Germantown, Md.) and eluted in a 30 μl volume. The 3' labeling reaction was done by using Taq polymerase (NEB) in the presence of alpha-$^{33}$P dATP according to standard protocols. Approximately 10 pmol of substrate was incubated with 1 unit of AbaSDFI in buffer 4 in 37° C. for 1 hour. 2 μl of the reaction, along with markers, was loaded onto 20% polyacrylamide gel with 7M urea. Markers were made synthetically and labeled with gamma-$^{33}$P ATP using T4 polynucleotide kinase (NEB). The gel was dried, exposed to phosphoscreen and scanned. The results are shown in FIG. 8B. In FIG. 8B, the cleavage sites can be deduced to be 12-13 nucleotides from the hmC in the same strand.

Although specific-sized cleavage fragments predominated in FIGS. 8A and 8B, it was found that sequence context and enzyme concentration may introduce a wobble at the enzyme cleavage site such that the cleavage sites might vary by one or two nucleotides.

Example 4

Determination of Whether ghmC has a Different or Similar Effect to hmC on Cleavage Patterns Using the methods described above, the cleavage specificity was compared for sites modified by hmC and ghmC.

All oligonucleotides with fluorescent labels and hmC were made through organic synthesis, as described above. The hmC-containing substrates were converted to ghmC-containing substrates using T4 BGT (NEB) according to the manufacturer's instructions. The results in FIG. 8C showed that hmC-containing DNA in lanes 1 and 3 had the same cleavage distance specificity as ghmC in lanes 2 and 4.

Example 5

Cloning of hmC Fragments from Rat Brain Genomic DNA

The utility of ZZYZ enzymes in discovering hmC sites in rat brain genomic DNA was tested. 1 μg of rat brain genomic DNA was first treated with T4 BGT to convert hmC to ghmC. The DNA was precipitated after the reaction and was subject to AbaSDFI-digestion. The digested DNA products were purified again and put into the ligation reaction with a synthetic dsDNA adaptor. One end of the adaptor had a 3' overhang with two degenerate bases so that it could ligate to the ends of the cleavage products with a 2-base 3'-overhang. The ligated products were then run on a low-melting agarose gel and size-selected from 1 kb-3 kb. The size-selected DNA was then PCR-amplified using a primer specific to the ligated adaptor. The PCR primer can be designed to have multiple restriction sites. In this example, XbaI was used to facilitate cloning. The PCR products were purified and digested with XbaI and ligated to a compatible vector for transformation. Colonies were grown and sequenced to determine the cloned inserts.

Figure 10:
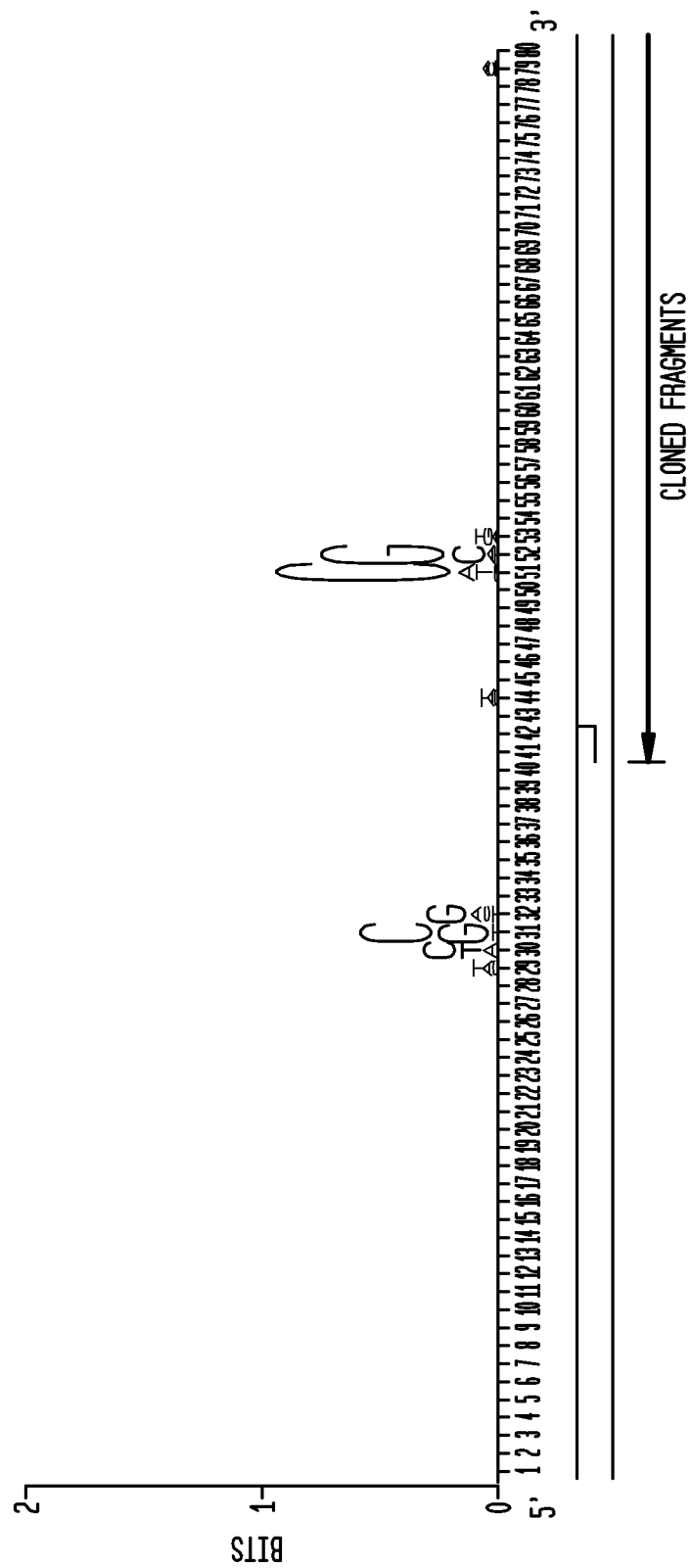
FIG. 10 shows a sequence logo representation of the cloned fragments from rat brain genomic DNA obtained according to FIG. 9. All cloned fragments were matched to the reference rat genome. The 40-bp window left and right of the cleavage site were extracted and aligned, as illustrated in the Figure.

In the subsequent computational analysis, sequences of the cloned inserts were all matched to the reference rat genome. The ends of these sequences signified the 2-bp 3'-overhang which AbaSDFI generated. We then extracted a 40-bp sequence window both left and right around the cleavage sites and aligned the sequences to reveal potential consensus, as shown in FIG. 10. Two prominent CG clusters were observed at both right and left side of the cleavage site. The distance between these CG clusters and the cleavage site matched the cleavage distances of the AbaSDFI enzyme. While not wishing to be limited to theory, it is proposed that dimerization of AbaSDFI may occur resulting in cleavage distances of about 22 nucleotides on one side of the modified cytosine. Thus, it can be concluded that at least one of the CG sites is hydroxymethylated.

Example 6

Detection of Hydroxymethylated Bases in Genomic DNA

E14 mouse embryonic stem cells and NIH3T3 mouse genomic DNA ~500 ng were subjected to digestion with an increased concentration of PvuRts1I at 25° C. for an hour in NEB4 buffer. The molecular weight markers were pBR322 DNA-digested with MspI, with the size of some of the bands listed on the right. The digested products were resolved on a 20% TBE gel for 2 hrs at 140 V, stained with SYBER® Gold nucleic acid gel stain (Invitrogen, now Life Technologies, Carlsbad, Calif.) and quantitated using a Typhoon scanner (GE Healthcare Life Sciences, Piscataway, N.J.) using 488 nM laser (see FIG. 15).

Example 7

Mapping Sequences Containing hmCs

When hmC occurs in the genome, it appears to commonly occur at a CpG site. However, it is also likely that the DNA is hemi-hydroxymethylated at that CpG site. If there are two neighboring CpG sites in a DNA sequence and the cleavage pattern suggests hemi-hydroxymethylation, it may be necessary to establish which of the two possible CpGs is hydroxymethylated. The following experiment illustrates how the location of a hemi-hydroxymethylated site can be established even when there are two neighboring CpGs.

Figure 11:
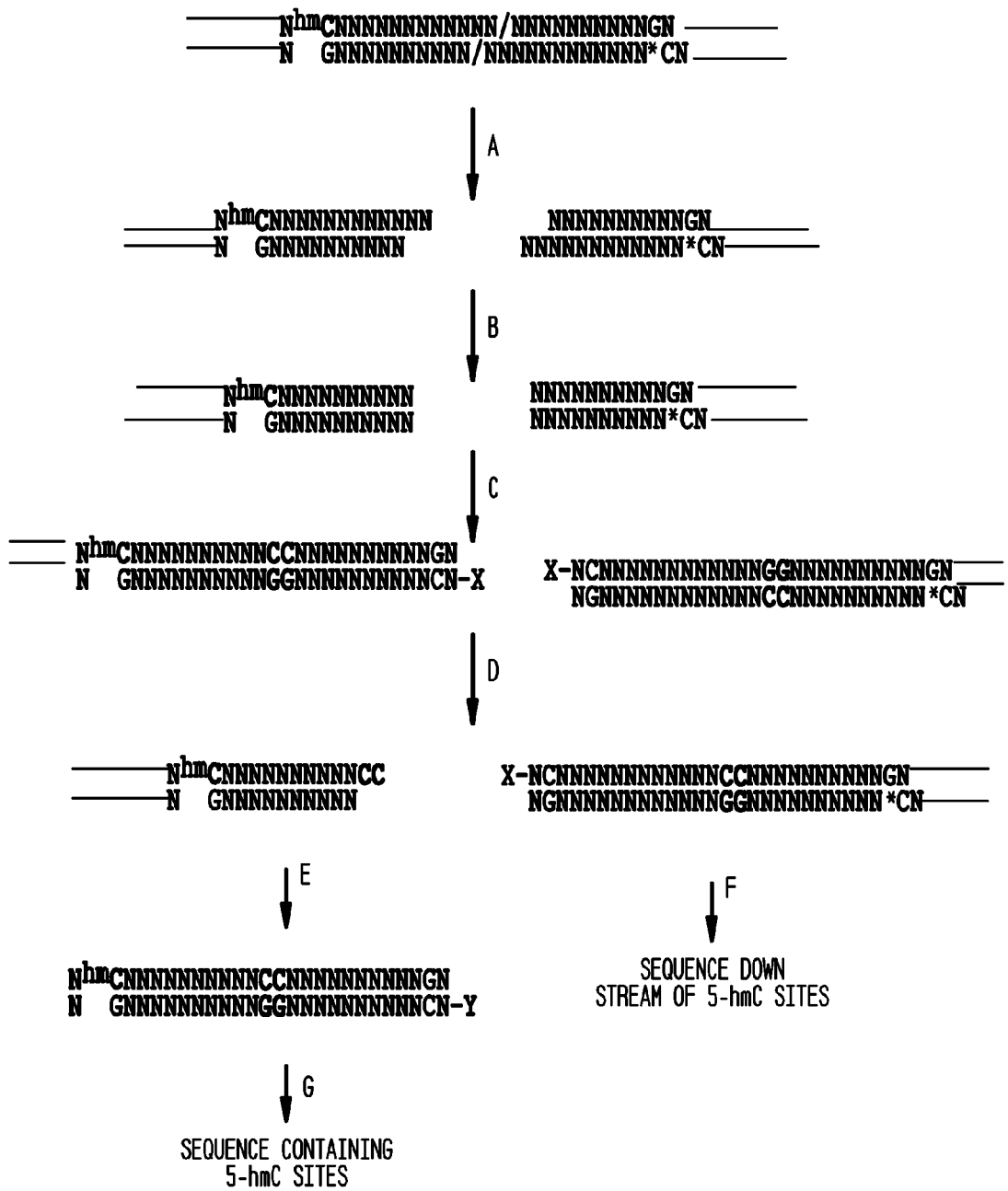
FIG. 11 describes a protocol for high throughput sequencing to determine which of the cytosines, in adjacent CpG motifs, is hemi-hydroxymethylated and serves as a substrate for ZZYZ family member cleavage. (A): Free ends of the DNA fragment for interrogation are blocked. Cleavage occurs at a site located between the two identified cytosines with an ZZYZ enzyme resulting in 1-3 base overhang. (B): The overhang is removed by blunt-ending. (C): An adapter of known sequence is ligated to the blunt end of both cleavage fragments where the adapter has an unmodified CC/GG at one end and a marker –X at the other. Unligated adapter is removed by spin column. (D): The adapter ligated DNA is cleaved a second time with the ZZYZ enzyme to liberate the adapter leaving behind the CC as an overhang from the fragment containing the hmC. The fragment that contains unmodified cytosine is not cleaved. Spin column is used to remove the cleaved adapter. (E): A second adapter is added to the cleaved fragment with the CC overhang. The second adapter carries a Y marker. The cytosine which is modified can be determined from sequencing the fragment with the Y marker. The unmodified cytosine can be verified by sequencing the fragment with the X marker. (F): The uncleaved fragment is sequenced downstream of the hmC (5-hmC) sites. (G): The hemi-hmC (5-hmC) is mapped on the reference genome.
Figure 12:
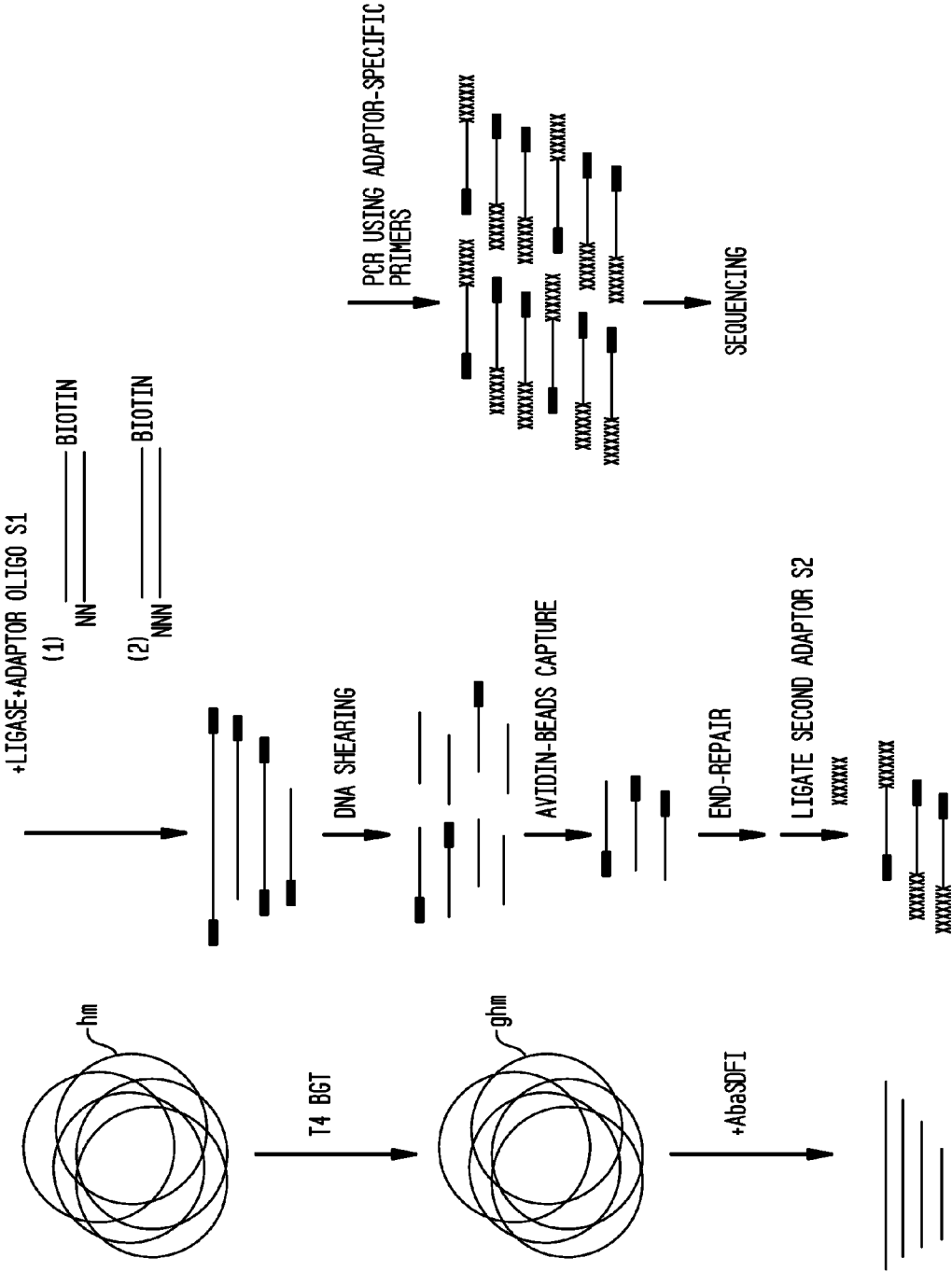
FIG. 12 shows an example of a sequencing pipeline for decoding a hydroxymethylome. Genomic DNA is first treated with BGT and then digested with a ZZYZ family enzyme (e.g., AbaSDFI). Individual adaptors, either with a 2-degenerate base 3' overhang or with a 3-degenerate base 3' overhang are then ligated to the digested products. The adaptor DNA has a label (such as biotin) to facilitate downstream purification. Ligated DNA is sheared to smaller fragments. Those fragments with adaptors ligated to the ends are pulled out using avidin beads. Fragments are then ligated with second sequencing adaptor. Ligated products are PCR-amplified using specific primers for sequencing.
Figure 14:
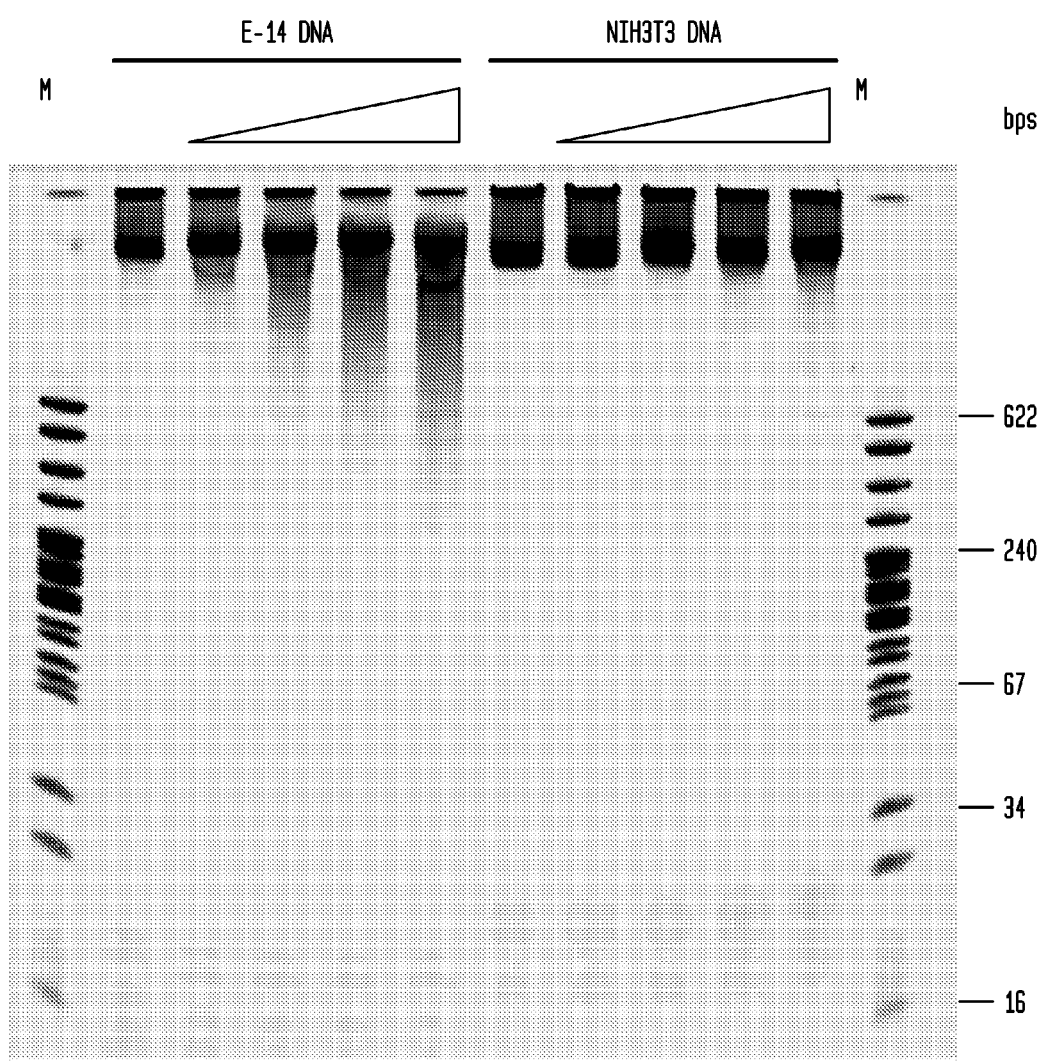
FIG. 14 shows that PvuRts1I can distinguish DNAs with different levels of hmC in different cells. Here the levels of hmC in embryonic stem cells were compared with fibroblasts. The E-14 genomic DNA was digested into a significant smear while the NIH3T3 DNA was digested only a little, confirming the significant presence of hemi-methylated hmC in E-14 cells and the significantly lower levels of any hmC in fibroblasts.

DNA fragments are created after specific or non-specific cleavage of a genome. Existing free ends on these fragments are blocked by, for example, blunting and dephosphorylation. The cleavage fragments are ligated to adapter oligonucleotides. The fragments are then subjected to cleavage by an enzyme from the ZZYZ family (for example, AbaSDF1). To determine whether DNA on both sides of a cleavage site contains an hmC or only one side has a hmC, digested genomic DNA is blunted and ligated to an X-bar-coded SOLiD primer and P1 primer using NEBNext® quick ligation module (NEB M2200). After ligation, the DNA is digested by the ZZYZ family of enzymes again, and the fragments that cannot be digested away from the X-bar-coded SOLiD™ primer (Applied Biosystems, now Life Technologies, Carlsbad, Calif.) will contain the sequence downstream of the hmC. The fragments that can be digested will produce a product with a specific 2 nt 3' end which is from the X-bar-coded primers. Then a second Y-bar-coded SOLiD™ primer is ligated to the free ends; this round of SOLiD™ sequencing will reveal the sequence containing the hmC. It does not matter if the 5-hmC sites are clustered or distributed randomly for this method (FIG. 11).

Determination of the position of hmC in a DNA sequence and mapping the sequence onto a genome map enables the creation of a hydroxymethylome. It also enables a diagnostic test to determine the presence of hmC on a target DNA and then to compare this to a reference hydroxymethylome to establish a correlation with a phenotype. is. By the specific enzyme digestion with or without glucosylation, coupled with qPCR, quantitation of the hydroxymethylation at specific sites can be determined.

Identifying the position and quantity of the hmC from different sources, including different tissues, and cell culture at different time points, can provide important insights into gene expression and regulation.

Example 8

A Method of Detecting hmC in a Sample of DNA

The characterization of the ZZYZ family of proteins opens new possibilities for the rapid analysis of large numbers of patient samples or a diagnostic test administered in the doctor's office.

Once hmCs are mapped on a hydroxymethylome and selected positions of hmC correlated to a phenotype, it will be desirable to determine the presence of specific hmCs in targeted regions of the genome. This can be readily achieved using an enzyme from the ZZYZ family of proteins. If the DNA is symmetrically hydroxymethylated, a specific sized fragment will result (20-23 nt). If the DNA is hemi-hydroxymethylated, the presence of hmC can be determined as indicated below.

A genomic DNA is optionally glucosylated and then subjected to an enzyme from the ZZYZ family of proteins in a suitable buffer such as 250 mM potassium acetate to permit cleavage into fragments at a site 11-13 nucleotides 3' downstream from the hmC on the same strand and 9-10 nucleotides 3' downstream from the hmC on the complementary strand. Primers are selected which are complementary to sequences on either side of the ZZYZ protein cleavage site such that the DNA that is not cleaved is amplified. The detected fragments will then correspond to an absence of hmC. Where the DNA is cleaved by a ZZYZ protein indicating the presence of hmC, no amplification product would be detected. By comparing the amplification product in geonomic samples treated and untreated with ZZYZ protein, one can potentially estimate the percentage of hydroxymethylation. Alternatively, adaptors containing a primer sequence can be ligated to the staggered ends at the 3' cleavage site or ligated to blunt-ended DNA and only those fragments having an hmC will be amplified by primer-dependent amplification. Thus, the presence of hmC will be detected as an amplification product. The amplified fragments in this case may be sequenced.

An advantage of the above method is that the entire reaction may be carried out in a single reaction vessel or microfluidic device or chip.

Example 9

Kit for Detecting hmC in a DNA Sample

A kit is provided which contains one or more purified recombinant proteins of a ZZYZ family of proteins, functional derivatives thereof or catalytic fragments thereof, for example AbaSDF1, together with a suitable reaction buffer and additionally a BGT and UDP-glucose. Additionally, a kit may contain oligonucleotide adapters to facilitate high throughput sequencing. Additionally, the kit may further comprise enzymes suitable for blunt-ending and ligation and in additional embodiments may include specific primers. In an embodiment of the invention, the kit further includes packaging materials and instructions therein to use the kits.

What is claimed is:

1. A method of detecting hydryoxymethyl cytosine (hmC) in a genomic DNA sample, comprising:
   (a) making a preparation comprising:
      (i) the genomic DNA sample;
      (ii) one or more purified recombinant proteins having at least 95% sequence identity to an amino acid sequence selected from the group consisting of BmeDI as set forth in SEQ ID NO: 5, BbiDI as set forth in SEQ ID NO: 6, AbaSDFI as set forth in SEQ ID NO: 7, PatTI as set forth in SEQ ID NO: 8, YkrI as set forth in SEQ ID NO: 9, SpeAI as set forth in SEQ ID NO: 10, EsaNI as set forth in SEQ ID NO: 11, and PpeHI as set forth in SEQ ID NO: 12;
      (iii) a reaction buffer;
   (b) permitting the protein to cleave the genomic DNA at a cleavage site;
   (c) determining the DNA sequence at least on one side of the cleavage site;
   (d) optionally mapping the DNA sequence onto a reference genomic DNA sequence; and
   (e) detecting the hmC.

2. The method according to claim 1, wherein the preparation in (a) further comprising: one or more of a DNA polymerase, primers and adapters.

3. The method according to claim 1, further comprising: amplifying the cleaved genomic DNA in (b) prior to determining the DNA sequence in (c).

4. The method according to claim 1, wherein the genomic DNA is reacted with a β-glucosyl transferase (BGT) prior to (a).

5. The method according to claim 1, further comprising: carrying out steps (a)-(c) in a single reaction vessel or microfluidic device.

6. The method according to claim 1, wherein the one or more purified proteins preferentially bind to a hydroxymethylated cytosine (hmC) and to a glucosylated hydroxymethylated cytosine (ghmC) in a DNA.

7. The method according to claim 1, wherein the one or more purified proteins preferentially cleave DNA at a defined distance 3' of the hmC or ghmC.

8. The method according to claim 7, wherein the defined distance is 11-13 nucleotides on the strand having the hmC or ghmC or 9-10 nucleotides on the complementary strand.

9. The method according to claim 7, wherein the one or more purified proteins cleave DNA having ghmC, hmC and/ or mC at a ratio of at least 8:1 of ghmC or hmC to methylated cytosine (mC).

10. The method according to claim 1, wherein the buffer comprises a salt characterized by an anion selected from the group consisting of a sulfate, a phosphate, an acetate and a citrate.

11. The method according to claim 10, wherein the buffer does not include a chloride, nitrate, carbonate or imidazole salt.

12. The method according to claim 10, wherein the salt concentration is 50-500 mM.

13. The method according to claim 1, wherein the at least one of the purified proteins is selected from the group consisting of: PvuRts1I, PpeHI, EsaSS310P, EsaRBORFBP, PatTI, YkrI, EsaNI, SpeAI, BbiDI, PfrCORF1I80P, PcoORF314P, BmeDI, AbaSDFI, AbaCI, AbaAI, AbaSI, AbaUMB3ORFAP and Asp6ORFAP and catalytically active mutants and derivatives thereof.

* * * * *

SEQUENCE LISTING

<160> NUMBER OF SEQ ID NOS: 16

<210> SEQ ID NO 1
<211> LENGTH: 948
<212> TYPE: DNA
<213> ORGANISM: artificial
<220> FEATURE:
<223> OTHER INFORMATION: oligonucleotide

<400> SEQUENCE: 1

| | | | | | |
|---|---|---|---|---|---|
| ttttaaatta | aaaatgaagt | tttaaatcaa | tctaaagtat | atatgagtaa | acttggtctg | 60 |
| acagttacca | atgcttaatc | agtgaggcac | ctatctcagc | gatctgtcta | tttcgttcat | 120 |
| ccatagttgc | ctgactcccc | gtcgtgtaga | taactacgat | acgggagggc | ttaccatctg | 180 |
| gccccagtgc | tgcaatgata | ccgcgagacc | cacgctcacc | ggctccagat | ttatcagcaa | 240 |
| taaaccagcc | agccggaagg | gccgagcgca | gaagtggtcc | tgcaacttta | tccgcctcca | 300 |
| tccagtctat | caattgttgc | cgggaagcta | gagtaagtag | ttcgccagtt | aatagtttgc | 360 |
| gcaacgttgt | tgccattgct | acaggcatcg | tggtgtcacg | ctcgtcgttt | ggtatggctt | 420 |
| cattcagctc | cggttcccaa | cgatcaaggc | gagttacatg | atcccccatg | ttgtgcaaaa | 480 |
| aagcggttag | ctccttcggt | cctccgatcg | ttgtcagaag | taagttggcc | gcagtgttat | 540 |
| cactcatggt | tatggcagca | ctgcataatt | ctcttactgt | catgccatcc | gtaagatgct | 600 |
| tttctgtgac | tggtgagtac | tcaaccaagt | cattctgaga | atagtgtatg | cggcgaccga | 660 |
| gttgctcttg | cccggcgtca | atacgggata | ataccgcgcc | acatagcaga | actttaaaag | 720 |
| tgctcatcat | tggaaaacgt | tcttcggggc | gaaaactctc | aaggatctta | ccgctgttga | 780 |
| gatccagttc | gatgtaaccc | actcgtgcac | ccaactgatc | ttcagcatct | tttactttca | 840 |
| ccagcgtttc | tgggtgagca | aaaacaggaa | ggcaaaatgc | cgcaaaaaag | ggaataaggg | 900 |
| cgacacggaa | atgttgaata | ctcatactct | tcctttttca | atattatt | | 948 |

<210> SEQ ID NO 2
<211> LENGTH: 56
<212> TYPE: DNA
<213> ORGANISM: artificial
<220> FEATURE:
<223> OTHER INFORMATION: oligonucleotide

<400> SEQUENCE: 2 cggcgttttcc gggttccata ggctccgcca cgtactctga tgaccagggc atcaca    56

<210> SEQ ID NO 3
<211> LENGTH: 55
<212> TYPE: DNA
<213> ORGANISM: artificial
<220> FEATURE:
<223> OTHER INFORMATION: oligonucleotide

<400> SEQUENCE: 3
ccatacatat cccttacttc tcctaacgtg gatgataaag gtagtttatg tggaa    55

<210> SEQ ID NO 4
<211> LENGTH: 55
<212> TYPE: DNA
<213> ORGANISM: artificial
<220> FEATURE:
<223> OTHER INFORMATION: oligonucleotide

<400> SEQUENCE: 4
tccacataaa ctacctttat catccacgtt aggagaagta agggatatgt atgga    55

<210> SEQ ID NO 5
<211> LENGTH: 334
<212> TYPE: PRT
<213> ORGANISM: Bacillus megaterium

<400> SEQUENCE: 5

Met Asn Lys Tyr Asp Tyr Ile Lys Arg Gln Leu Ala Lys Thr Asn Lys
1               5                   10                  15

Lys Asn Asp Glu Asn Tyr Ile Val Thr Arg Ile Trp His Leu Leu Asp
                20                  25                  30

Asn Tyr Asp Ile Lys Ile Asn Thr Gln Gln Tyr Val Val Arg Ser Asn
            35                  40                  45

Lys Asn Gln Lys Ala Glu Tyr Gly Leu Ile Asp Leu Tyr Phe Pro Gln
    50                  55                  60

Phe Asn Leu Ala Val Glu Ile Asp Glu Ala His His Lys Asn Asp Ile
65                  70                  75                  80

Asn Gln Thr Leu Asp Glu Ile Arg Lys Asn Asp Ile Val Asn Ala Leu
                85                  90                  95

Asp Cys Glu Phe Ile Arg Ile Asp Ala Thr Gln Ser Phe Glu Lys Ile
            100                 105                 110

His Glu Lys Ile Asp Gln Val Val Glu Lys Ile Asn Leu Leu Thr Lys
    115                 120                 125

Glu Lys Trp Phe Ile Pro Trp Asp Leu Glu Lys Glu Tyr Asp Pro Asn
130                 135                 140

Thr Tyr Ile Glu Gln Gly Tyr Ile Asp Ala Asp Asp Asn Val Ser Leu
145                 150                 155                 160

Arg Leu Val Ala Asp Cys Cys Asn Val Phe Gly Ala Gly Tyr Ala His
                165                 170                 175

Gly Ile Gln Lys Ser Gly Ala Pro His Lys Phe Glu Asp Thr Asp
            180                 185                 190

Ile Lys Arg Leu Lys Phe Phe Pro Asn Glu Thr Trp Asn Asn Gln Leu
    195                 200                 205

Leu Glu Asn Glu Glu Ile Phe Ile Glu Tyr Asn Thr Ile Pro Glu Glu
210                 215                 220

Asn Glu Ala Tyr Phe Gln Lys Arg Met Tyr Gln Leu Asn Gln Lys Ile
225                 230                 235                 240

Ala Leu Phe Ala Tyr Ala Lys Thr Ser Ser Gly Arg Phe Glu Ala Ile
                245                 250                 255

Phe Lys Gly Leu Tyr Leu Leu Asn Arg Glu Lys Ser Lys Asn Thr Gly
            260                 265                 270

Val Leu Thr Tyr Asn Arg Ile Ser Thr Ile Met Pro Thr Tyr Tyr Pro
    275                 280                 285

Lys Asp Val Lys Gln Pro Leu Arg Ile Ala Glu Ala Tyr Asn Asn Asp
290                 295                 300

Glu Tyr Lys Val Ala His Phe Tyr Thr Glu Asn Gln Val Arg Lys Phe
305                 310                 315                 320

Glu Gly Lys Tyr Lys Lys Arg Tyr Lys Ile Ile Ser Tyr Ser
                325                 330

<210> SEQ ID NO 6
<211> LENGTH: 309
<212> TYPE: PRT
<213> ORGANISM: Bifidobacterium bifidum

<400> SEQUENCE: 6

Met Ser Gly Ala Asp Lys Leu Gly Tyr Leu Ile Arg Ala Leu Ser Arg
1               5                   10                  15

Thr Lys Arg Lys Asp Tyr Glu Asn Tyr Val Val Asn Ala Ile Trp Asn
                20                  25                  30

Arg Leu Ala Met Asp Asp Val Lys Pro Val Thr Gln Gln Leu Val Leu
            35                  40                  45

Trp Pro Asp Gly Arg Arg Ser Phe Val Asp Leu Tyr Phe Pro Gln Ala
    50                  55                  60

Met Ile Gly Val Glu Cys Asp Glu Ala Tyr His Gln Arg Gln Arg Glu
65                  70                  75                  80

Arg Asp Arg Glu Arg Glu Ile Thr Ile Thr Asp Val Leu Arg Gln Ile
                85                  90                  95

Arg Gly Glu Asp Tyr Arg Ala Leu His Val Asp Val Ser Gly Ser Tyr
            100                 105                 110

Glu Gln Val Glu Arg Ser Ile Asp Asp Cys Val Arg Arg Ile Arg Ala
            115                 120                 125

Glu Ile Glu Arg Arg Gln Ala Asn Glu Phe Thr Pro Trp Thr Glu
130                 135                 140

Ala Tyr Val Asp Tyr Lys Glu Phe Tyr Lys Thr Arg Asp Ala Val Ser
145                 150                 155                 160

Val Ala Asp Asp Val Gly Phe Pro Arg Ile Ala Asp Ala Val Asn Thr
                165                 170                 175

Leu Cys Gly Ser Glu Tyr Lys Arg Phe Gln Glu Ser Trp Phe Val Pro
            180                 185                 190

Ser Val Met Arg Gln Trp Tyr Gly Asp Arg Tyr Arg Val Trp Phe Pro
            195                 200                 205

Lys Leu Ala Ile Gly Gly Lys Ala Val Ala Asn Gly Trp Asn Asn Arg
    210                 215                 220

Leu Ser Asp Asp Gly Thr Tyr Ile Tyr Glu Tyr Asn Glu Asp Ala Asp
225                 230                 235                 240

Leu Val Asp Pro Val Gly Asp Gly Asp Pro Asn Asp Ile Arg Ile Thr
                245                 250                 255

Phe Ala Lys Ser Ala Asp Pro Val Thr Arg Ile Gln Ala Tyr Arg Phe
            260                 265                 270

Val Gly Val Phe Arg Arg Ile Ser Asn Ser Glu Asp Gly Thr Arg Lys
            275                 280                 285

Arg Tyr Gln Arg Ile Glu Thr Val Phe Pro Ile His Arg Thr Pro Cys
    290                 295                 300

Leu Pro Ile His Arg
305

<210> SEQ ID NO 7
<211> LENGTH: 321
<212> TYPE: PRT
<213> ORGANISM: Acinetobacter baumannii

<400> SEQUENCE: 7

Met Cys Asn Lys Ala Ser Ser Asp Leu Thr Asp Tyr Val Ile Arg Gln
1               5                   10                  15

Leu Gly Arg Thr Lys Asn Lys Arg Tyr Glu Ala Tyr Val Val Ser Arg
                20                  25                  30

Ile Ile His Leu Leu Asn Asp Phe Thr Leu Lys Phe Val Thr Gln Gln
            35                  40                  45

Phe Val Arg Leu Ser Asn Lys Lys Ile Ala Leu Thr Asp Leu Tyr Phe

```
                  50                  55                  60
Pro Gln Leu Gly Ile His Ile Glu Val Asp Glu Gly His His Phe Leu
 65                  70                  75                  80

Arg Asn Ser Lys Met Glu Tyr Ser Leu Asn Gln Ile Asp Glu Pro Leu
                 85                  90                  95

Tyr Ser Ile Ser Gln Thr Glu Ser Asp Ala Met Arg Glu Glu Asp Ile
                100                 105                 110

Ile Ser Ile Thr Gly His Lys Ile Phe Arg Val Asn Val Phe Lys Asn
                115                 120                 125

Gln Glu Gly Gln Pro Gln Asn Leu Glu Asn Ile His Gln Gln Ile Asp
130                 135                 140

Lys Ile Ile Glu Glu Ile Lys Thr Ala Lys Asn Lys Leu Ile Glu Ala
145                 150                 155                 160

Ser Thr Phe Lys Glu Trp Asn Ile Glu Thr Glu Tyr Asn Pro Gln Thr
                165                 170                 175

Tyr Ile Asp Leu Gly Arg Ile Ser Leu Ala Asp Asn Val Val Leu Lys
                180                 185                 190

Thr Thr Lys Asp Val Cys Asn Cys Phe Gly Tyr Ser Tyr Lys Asn Tyr
                195                 200                 205

Gln Arg Gly Gly Ala Leu His Pro Tyr Lys Asp Thr Leu Ile Trp
210                 215                 220

Phe Pro Arg Leu Tyr Glu Asn Lys Asp Trp Ile Asn Thr Ile Ser Pro
225                 230                 235                 240

Asp Gly Leu Thr Ile Thr Glu Lys Ser Thr Asp Glu Thr Ile Thr Leu
                245                 250                 255

Lys Lys Leu Glu Glu Trp Lys Asn Gly Pro Gln Lys Arg Ile Val Phe
                260                 265                 270

Ala Arg Val Lys Asp Asn Leu Ser Ser Arg Ala Met Tyr Arg Phe Met
                275                 280                 285

Gly Leu Tyr Glu Phe Gln Lys Ala Asp Leu Lys Asp Gly Ala Val Trp
                290                 295                 300

Lys Arg Val Lys Cys Glu Val Gln Thr Tyr Ser Pro Lys Glu Thr Lys
305                 310                 315                 320

Cys

<210> SEQ ID NO 8
<211> LENGTH: 285
<212> TYPE: PRT
<213> ORGANISM: Pseudoalteromonas atlantica

<400> SEQUENCE: 8

Met Asp Lys Lys Glu Tyr Ile Ile Arg Gln Leu Gly Arg Thr Lys Asn
 1               5                  10                  15

Lys Lys Tyr Glu Ala Tyr Val Val Thr Arg Ile Ile His Leu Leu Asn
                20                  25                  30

Asp Phe Ser Ile Lys Phe Ile Thr Gln Gln Tyr Val Thr Arg Pro Lys
            35                  40                  45

Gly Arg Ala Leu Thr Asp Leu Tyr Phe Pro Gln Phe Ala Phe His Ile
 50                  55                  60

Glu Val Asp Glu Gly Gln His Phe Asn Gln Ala Asn Ile Glu Ala Asp
 65                  70                  75                  80

Lys Ile Arg Glu Ala Asp Ile Ile Asn Ala Thr Gly His Glu Ile Leu
                 85                  90                  95

Arg Ile Asp Val Thr Lys Ser Phe Asp Asp Ile Asn Thr Gln Ile Asp
```

```
            100                 105                 110
Ala Ala Val Asn Lys Ile Lys Ser Met Arg Gln Glu Ile Ser Phe Ile
        115                 120                 125

Pro Trp Asp Ile Asp Ser Glu Phe Asp Ser Ala Thr Tyr Ile Lys Arg
    130                 135                 140

Gly Tyr Ile Asp Ile Lys Asp Asn Val Ala Phe Lys Thr Ile Lys Asp
145                 150                 155                 160

Ala Cys Asn Cys Phe Gly His Asn Tyr Thr Gly Tyr Gln Arg Ala Gly
                165                 170                 175

Ala Ala His Pro Asp His Tyr Ile Met Leu Trp Phe Pro Lys Leu Phe
            180                 185                 190

Pro Asn Gly Glu Trp Asp Asn Gln Ile Ser Ser Asp Glu Glu Val Ile
        195                 200                 205

Thr Glu Arg Asn Glu Asp Asp Lys Lys Ala Lys Gln His Val Ser Ser
    210                 215                 220

His Val Asn Asn Lys Glu Lys His Lys His Gln Arg Ile Val Phe Ala
225                 230                 235                 240

Lys Val Arg Gly Asn Leu Gly Asp Val Leu Tyr Arg Phe Arg Gly Gln
                245                 250                 255

Tyr Gln Leu Asp Val Lys Asp Ser Asn Glu Lys Thr Gly Leu Ile Trp
            260                 265                 270

Arg Arg Ile Lys Thr Arg Val Lys Thr Tyr Glu Gln Asn
        275                 280                 285

<210> SEQ ID NO 9
<211> LENGTH: 289
<212> TYPE: PRT
<213> ORGANISM: Yersinia kristensenii

<400> SEQUENCE: 9

Met Ile Ser Gln Tyr Glu Tyr Val Val Arg Gln Leu Ala Arg Thr Lys
1               5                   10                  15

Asn Lys Lys His Glu Gln Tyr Val Val Thr Gly Ile Val His Lys Leu
            20                  25                  30

Asn Arg Asp Asp Ile Lys Phe Val Thr Gln Gln Tyr Val Lys Arg Glu
        35                  40                  45

Ser Gly Arg Ala Leu Thr Asp Leu Tyr Phe Pro Ala Ile Asn Leu His
    50                  55                  60

Ile Glu Ile Asp Glu Pro Phe His Leu Lys Gln Ala Glu His Asp Asn
65                  70                  75                  80

Leu Arg Glu Ala Asp Ile Ile Asp Ala Thr Gly His Glu Val Ile Arg
                85                  90                  95

Ile Ser Val Asp Gly Ser Leu Arg Gln Met Asn Glu Arg Ile Asp Asp
            100                 105                 110

Cys Val Ala Ala Ile Lys Ser Lys Ile Ser Ala Leu Gly Asp Cys Phe
        115                 120                 125

Glu Pro Trp Asp Met Asp Lys Glu Leu Ser Ile Glu Pro His Ile Arg
    130                 135                 140

Arg Gly Tyr Ile Asp Val Lys Asp Asn Val Ala Phe Arg Arg Ile Thr
145                 150                 155                 160

Asp Ala Cys Asn Cys Phe Gly His Asn Tyr Lys Phe Leu Gln Lys Ala
                165                 170                 175

Gly Ala Lys His Pro Tyr His Asp Asp Ile Leu Ile Trp Leu Pro Lys
            180                 185                 190
```

```
Leu Phe Asp Asn Glu His Trp Ser Asn Gln Ile Ser Asn Asp Glu Asn
            195                 200                 205

Val Ile Thr Glu Ile Pro Lys Ser Glu Asp Ala Gln Ala Ala His Phe
    210                 215                 220

Asp Lys Trp Met Ala Glu Thr Arg Asn Lys Arg Leu Val Phe Ala Lys
225                 230                 235                 240

Ala Lys Asp Asn Leu Gly Met Thr Leu Tyr Arg Phe Lys Gly Leu Tyr
                245                 250                 255

Glu Leu Asn Pro Lys Lys Ser Asn Arg Thr Ile Gly Leu Tyr Trp Gln
            260                 265                 270

Arg Ile Ser Thr Arg Val Lys Thr Tyr Pro Ser Pro Ala Arg Asn Pro
        275                 280                 285

Asp

<210> SEQ ID NO 10
<211> LENGTH: 283
<212> TYPE: PRT
<213> ORGANISM: Shewanella pealeana

<400> SEQUENCE: 10

Met Lys Thr Leu His Met Thr Arg Gln Leu Gln Arg Cys Lys Asn Lys
1               5                   10                  15

Arg Phe Glu Leu Tyr Ala Ile Thr Arg Ile Ile His Lys Val Asp Asp
            20                  25                  30

Leu Asp Ile Lys Phe Ile Thr Gln Gln Tyr Val Ala Arg Pro Asp Gly
        35                  40                  45

Phe Ala Leu Thr Asp Leu Tyr Leu Pro Gln Leu Lys Leu His Ile Glu
    50                  55                  60

Ile Asp Glu Gly Phe His Lys Gln Gln Val Asp Ala Asp Lys Val Arg
65                  70                  75                  80

Glu Leu Asp Ile Ile Thr Ala Thr Asp His Gln Val Lys Arg Ile Asp
                85                  90                  95

Ala Ser Val Ala Ile Glu Gln Ile Asn Leu Gln Val Asp Gln Ile Val
            100                 105                 110

Ala Glu Ile Leu Gln Ser Val Glu Val Gln Lys Ala Ala Gly Asn Phe
        115                 120                 125

Gln Ala Trp Asp Pro Glu Thr Glu His Ser Val Ser Tyr Leu Gln Ser
    130                 135                 140

Arg Gly Val Ile Arg Ala Ser Glu Asn Val Ala Leu Arg Thr Ser Ala
145                 150                 155                 160

Glu Val Cys Asn Leu Leu Gly His Asn Tyr Lys Gly Trp Gln Arg Ser
                165                 170                 175

Ser Ala Ser Val Pro His Tyr Pro Asn Ile Arg Leu Trp Phe Pro Lys
            180                 185                 190

Leu Tyr Pro Asn Glu Gln Trp Phe Asn His Ile Ser Tyr Asp Gly Cys
        195                 200                 205

Glu Ile His Glu Tyr Cys Ile Glu Ser Glu Thr Lys Lys Arg Gln Phe
    210                 215                 220

Ile Asp Lys Asn Leu Ser Glu Asn Ile Gln Gln Met Val Phe Ala Arg
225                 230                 235                 240

Val Lys Asp Glu Leu Gly Gln Thr Met Tyr Arg Phe Lys Gly Leu Phe
                245                 250                 255

Ile Leu Asp Arg Asp Lys Thr Cys His Glu Ser Gly Val Tyr Trp Lys
            260                 265                 270
```

```
Arg Val Ala Thr Glu Phe Glu Leu Gly Leu Thr
            275                 280
```

<210> SEQ ID NO 11
<211> LENGTH: 296
<212> TYPE: PRT
<213> ORGANISM: Unknown
<220> FEATURE:
<223> OTHER INFORMATION: Environmental sample, Newport Harbor, Rhode
      Island

<400> SEQUENCE: 11

```
Met Ser Lys Phe Thr Lys Glu Thr Tyr Val Thr Arg Asn Phe Gln Lys
1               5                   10                  15

Ile Ser Gly Lys Arg Trp Glu Leu Tyr Val Ile Thr Arg Val Ile His
            20                  25                  30

Leu Leu Asn Asp Pro Asp Ile Glu Tyr Val Cys Gln Gln Tyr Ile Asn
        35                  40                  45

Pro Pro Gln Asn Lys Asp Tyr Tyr Leu Ala Asp Leu Ala Phe Pro Ser
    50                  55                  60

Leu Lys Leu Tyr Leu Glu Ile Asp Glu Gly Gln His Gly Ser Glu Met
65                  70                  75                  80

His Gln Thr Ser Asp Leu Lys Arg Asp Ala Glu Ile Leu Glu Ala Thr
                85                  90                  95

Asp Trp Thr Cys Lys Arg Ile Pro Val Phe Val Lys Lys Gly Ser Ser
            100                 105                 110

Lys Ile Asp Lys Ser Leu Glu Ala Leu Asn Lys Glu Ile Asp Asp Phe
        115                 120                 125

Val Ser Tyr Val Glu Gln Lys Lys Gln Lys Met Val Ser Ala Gly His
    130                 135                 140

Lys Ile Ser Trp Asn Tyr Glu Gln Lys Phe Ser Pro Thr Phe Thr Phe Ile
145                 150                 155                 160

Ala Lys Glu Lys Ile Lys Val Ser Asp Asn Val Ala Leu Leu Asn His
                165                 170                 175

Arg Asp Val Leu Arg Leu Phe Gly Tyr Lys Lys Gly His Tyr Gln Arg
            180                 185                 190

Ala Val Trp Thr Ile Lys Lys Thr Asn Gln Met Val Trp Phe Pro Lys
        195                 200                 205

Leu Tyr Pro Asn Ser Asp Trp Val Asn Ser Phe Asp Asp Lys Ser Gly
    210                 215                 220

Tyr Ile His Gln Phe Arg Lys Asp Asn Gln Pro His Pro Met Pro Lys
225                 230                 235                 240

Glu Gly Asp Pro Asp Arg Ile Val Phe Ala His Gln Lys Asn Ile Phe
                245                 250                 255

Gly Gln Thr Val Tyr Lys Phe Phe Gly Ile Phe Arg Ala Asp Leu Asn
            260                 265                 270

Lys Thr Asp Pro Val His His Tyr Phe Lys Arg Ile Asn Thr Cys Leu
        275                 280                 285

Asp Leu Ser Arg Tyr Ser Ala Asn
    290                 295
```

<210> SEQ ID NO 12
<211> LENGTH: 293
<212> TYPE: PRT
<213> ORGANISM: Proteus penneri

<400> SEQUENCE: 12

Met Ser Lys Thr Asp Tyr Ile Leu Arg Ser Leu Ser Lys Ile Thr Lys
1               5                   10                  15

Lys Arg Trp Glu His Tyr Val Ile Asn Arg Ile Phe His Lys Leu Asp
            20                  25                  30

Asp Pro Glu Ile Glu Phe Val Cys Gln Gln Cys Ile Arg Lys Ala Asn
                35                  40                  45

Ser Pro Asp Lys Ile Tyr Leu Ala Asp Leu Phe Phe Pro Gln Leu Ala
    50                  55                  60

Leu Tyr Leu Glu Ile Asp Glu His His Asp Ser Asp Glu Ala Lys
65                  70                  75                  80

Lys Lys Asp Ala Lys Arg Arg Leu Asp Ile Ile Glu Ala Thr Gly Phe
                85                  90                  95

Ile Glu Lys Arg Ile Pro Ala Ser Asn Val Thr Ile Glu Gln Leu Asn
                100                 105                 110

Thr Ser Ile Asp Glu Phe Val Lys Leu Leu Ile Asp Thr Lys Glu Lys
            115                 120                 125

Gln Lys Ala Gln Lys Lys Phe Ile Pro Trp Asp Tyr Ser Ala Gln Tyr
    130                 135                 140

Thr Ala Lys Arg His Ile Asp Ala Gly Phe Ile Glu Val Gly Pro His
145                 150                 155                 160

Ala Ile Phe Arg Tyr His Arg Asp Ala Leu Glu Cys Phe Gly Tyr Ile
                165                 170                 175

Asn Lys Gly His His Gln Ser Gly Ser Trp Lys Leu Pro Glu Asn Ile
            180                 185                 190

Val Arg Glu Ile Gly Leu Ser Gly Arg Ile Met Val Trp Phe Pro Arg
            195                 200                 205

Leu Tyr Asn Ala Gly Val Trp Asn Asn Glu Leu Ser Pro Asp Gly Glu
    210                 215                 220

Trp Ile Thr Glu Glu Ser Leu Glu Val Asp Asn Asn Tyr Ile Glu Asp
225                 230                 235                 240

Trp Asp Tyr Arg Ile Val Met Ala His Ser Arg Asp Glu Leu Asn Arg
                245                 250                 255

Val Leu Tyr Arg Phe Leu Gly Val Phe Gln Ile Asp Lys Asn Lys Ser
            260                 265                 270

Val Glu Gly Lys Asn Ile Phe Lys Arg Ile Asn Thr Lys Val Lys Val
            275                 280                 285

Phe Asn Ser Tyr Asn
            290

<210> SEQ ID NO 13
<211> LENGTH: 293
<212> TYPE: PRT
<213> ORGANISM: Proteus vulgaris

<400> SEQUENCE: 13

Met Ser Lys Thr Asp Tyr Ile Leu Arg Ala Leu Ser Lys Ile Ser His
1               5                   10                  15

Lys Arg Trp Glu His Tyr Ile Ile Asn Arg Val Val His Thr Leu Asp
            20                  25                  30

Asp Pro Asp Ile Glu Phe Val Cys Gln Gln Cys Ile Arg Lys Glu Gly
                35                  40                  45

His Leu Gly Lys Ile Tyr Leu Ala Asp Leu Leu Phe Pro Gln Leu Asn
    50                  55                  60

Leu Tyr Leu Glu Ile Asp Glu Ala His His Asp Ser Asn Asp Ala Arg
65                  70                  75                  80

Lys Ala Asp Ala Val Arg Arg Leu Asp Ile Val Glu Ala Thr Gly Phe
            85                  90                  95

Gln Glu Glu Arg Ile Pro Ala Ser Asn Ile Thr Leu Ser Glu Val Asn
           100                 105                 110

Lys Leu Val Asp Glu Phe Val Arg Leu Val Lys Asp Lys Lys Glu Glu
       115                 120                 125

Leu Glu Asn Gln Gly Leu Phe Phe Arg Trp Asp Tyr Asp Glu Arg Tyr
   130                 135                 140

Ser Ala Lys Lys His Ile Asn Thr Gly Tyr Met Ala Val Gly Pro Asn
145                 150                 155                 160

Ser Val Phe Arg Tyr His Arg Asp Ala Leu Gln Cys Phe Gly Tyr Arg
            165                 170                 175

Arg Glu Gly His His Gln Ser Gly Gly Trp Ala Leu Pro Ala Glu Val
        180                 185                 190

Ala Gln Ser Ile Gly Leu Thr Gly Arg Val Met Val Trp Phe Pro Arg
    195                 200                 205

Leu Tyr Glu Ala Gly Glu Trp Lys Asn Ala Leu Ser Ala Asp Gly Asn
    210                 215                 220

Lys Ile Thr Glu Gln Ser Leu Asn Ala Thr Arg Asn Tyr Gln Glu Thr
225                 230                 235                 240

Trp Asp Tyr Arg Ile Val Met Ala His Ser Arg Asp Glu Leu Asn Arg
            245                 250                 255

Thr Leu Tyr Arg Phe Leu Gly Val Phe Ala Ile Asp Val Asp Lys Ser
        260                 265                 270

Ser Asp Glu Val Lys Val Phe Ser Arg Val Tyr Ser Arg Val Asn Val
    275                 280                 285

Tyr Arg Ser Gln Asn
    290

<210> SEQ ID NO 14
<211> LENGTH: 102
<212> TYPE: PRT
<213> ORGANISM: artificial
<220> FEATURE:
<223> OTHER INFORMATION: consensus sequence in N-terminal domain
<220> FEATURE:
<221> NAME/KEY: MISC_FEATURE
<222> LOCATION: (2)..(8)
<223> OTHER INFORMATION: X =any amino acid
<220> FEATURE:
<221> NAME/KEY: MISC_FEATURE
<222> LOCATION: (10)..(11)
<223> OTHER INFORMATION: X=any amino acid
<220> FEATURE:
<221> NAME/KEY: MISC_FEATURE
<222> LOCATION: (13)..(13)
<223> OTHER INFORMATION: X=any amino acid
<220> FEATURE:
<221> NAME/KEY: MISC_FEATURE
<222> LOCATION: (15)..(32)
<223> OTHER INFORMATION: X=any amino acid
<220> FEATURE:
<221> NAME/KEY: MISC_FEATURE
<222> LOCATION: (35)..(50)
<223> OTHER INFORMATION: X=any amino acid and may be repeated as few as
    11 times and as much as 16 times
<220> FEATURE:
<221> NAME/KEY: MISC_FEATURE
<222> LOCATION: (53)..(54)
<223> OTHER INFORMATION: X=any amino acid
<220> FEATURE:
<221> NAME/KEY: MISC_FEATURE
<222> LOCATION: (56)..(61)
<223> OTHER INFORMATION: X=any amino acid -continued

```
<220> FEATURE:
<221> NAME/KEY: MISC_FEATURE
<222> LOCATION: (63)..(63)
<223> OTHER INFORMATION: X=any amino acid
<220> FEATURE:
<221> NAME/KEY: MISC_FEATURE
<222> LOCATION: (66)..(67)
<223> OTHER INFORMATION: X=any amino acid
<220> FEATURE:
<221> NAME/KEY: MISC_FEATURE
<222> LOCATION: (69)..(94)
<223> OTHER INFORMATION: X=any amino acid and may be repeated as few as
      6 times and as much as 26 times
<220> FEATURE:
<221> NAME/KEY: MISC_FEATURE
<222> LOCATION: (96)..(97)
<223> OTHER INFORMATION: X=any amino acid
<220> FEATURE:
<221> NAME/KEY: MISC_FEATURE
<222> LOCATION: (99)..(101)
<223> OTHER INFORMATION: X=any amino acid

<400> SEQUENCE: 14

Arg Xaa Xaa Xaa Xaa Xaa Xaa Lys Xaa Xaa Glu Xaa Tyr Xaa Xaa
 1               5                  10                  15

Xaa Xaa Xaa Xaa Xaa Xaa Xaa Xaa Xaa Xaa Xaa Xaa Xaa Xaa Xaa
             20                  25                  30

Gln Gln Xaa Xaa Xaa Xaa Xaa Xaa Xaa Xaa Xaa Xaa Xaa Xaa Xaa
         35                  40                  45

Xaa Xaa Asp Leu Xaa Xaa Pro Xaa Xaa Xaa Xaa Xaa Glu Xaa Asp
     50                  55                  60

Glu Xaa Xaa His Xaa Xaa Xaa Xaa Xaa Xaa Xaa Xaa Xaa Xaa Xaa
 65                  70                  75                  80

Xaa Xaa Xaa Xaa Xaa Xaa Xaa Xaa Xaa Xaa Xaa Xaa Xaa Asp Xaa
                 85                  90                  95

Xaa Arg Xaa Xaa Xaa Ile
            100

<210> SEQ ID NO 15
<211> LENGTH: 79
<212> TYPE: PRT
<213> ORGANISM: artificial
<220> FEATURE:
<223> OTHER INFORMATION: consensus sequence in the C-terminal
<220> FEATURE:
<221> NAME/KEY: MISC_FEATURE
<222> LOCATION: (2)..(2)
<223> OTHER INFORMATION: X=any amino acid
<220> FEATURE:
<221> NAME/KEY: MISC_FEATURE
<222> LOCATION: (4)..(43)
<223> OTHER INFORMATION: X=any amino acid; X may be repeated as few as
      30 times and as much as 40 times
<220> FEATURE:
<221> NAME/KEY: MISC_FEATURE
<222> LOCATION: (45)..(57)
<223> OTHER INFORMATION: X=any amino acid, X may be repeated as few as
      12 times and as much as 13 times
<220> FEATURE:
<221> NAME/KEY: MISC_FEATURE
<222> LOCATION: (59)..(59)
<223> OTHER INFORMATION: X=any amino acid
<220> FEATURE:
<221> NAME/KEY: MISC_FEATURE
<222> LOCATION: (61)..(78)
<223> OTHER INFORMATION: X=any amino acid, X may be repeated as few as
      16 times and as much as 18 times

<400> SEQUENCE: 15

Trp Xaa Asn Xaa Xaa Xaa Xaa Xaa Xaa Xaa Xaa Xaa Xaa Xaa Xaa
```

```
1               5                   10                  15
Xaa Xaa Xaa Xaa Xaa Xaa Xaa Xaa Xaa Xaa Xaa Xaa Xaa Xaa Xaa
        20                  25                  30
Xaa Xaa Xaa Xaa Xaa Xaa Xaa Xaa Xaa Ala Xaa Xaa Xaa Xaa
        35                  40                  45
Xaa Xaa Xaa Xaa Xaa Xaa Xaa Xaa Phe Xaa Gly Xaa Xaa Xaa Xaa
    50                  55                  60
Xaa Xaa Xaa Xaa Xaa Xaa Xaa Xaa Xaa Xaa Xaa Xaa Xaa Arg
65                  70                  75

<210> SEQ ID NO 16
<211> LENGTH: 102
<212> TYPE: PRT
<213> ORGANISM: artificial
<220> FEATURE:
<223> OTHER INFORMATION: consensus sequence in the N-terminal domain
<220> FEATURE:
<221> NAME/KEY: MISC_FEATURE
<222> LOCATION: (2)..(8)
<223> OTHER INFORMATION: X=any amino acid
<220> FEATURE:
<221> NAME/KEY: MISC_FEATURE
<222> LOCATION: (10)..(11)
<223> OTHER INFORMATION: X=any amino acid
<220> FEATURE:
<221> NAME/KEY: MISC_FEATURE
<222> LOCATION: (13)..(13)
<223> OTHER INFORMATION: X=any amino acid
<220> FEATURE:
<221> NAME/KEY: MISC_FEATURE
<222> LOCATION: (15)..(32)
<223> OTHER INFORMATION: X=any amino acid
<220> FEATURE:
<221> NAME/KEY: MISC_FEATURE
<222> LOCATION: (35)..(50)
<223> OTHER INFORMATION: X=any amino acid, X may be repeated as few as
      11 times and as much as 16 times
<220> FEATURE:
<221> NAME/KEY: MISC_FEATURE
<222> LOCATION: (53)..(54)
<223> OTHER INFORMATION: X=any amino acid
<220> FEATURE:
<221> NAME/KEY: MISC_FEATURE
<222> LOCATION: (56)..(61)
<223> OTHER INFORMATION: X=any amino acid
<220> FEATURE:
<221> NAME/KEY: MISC_FEATURE
<222> LOCATION: (63)..(63)
<223> OTHER INFORMATION: X=any amino acid
<220> FEATURE:
<221> NAME/KEY: MISC_FEATURE
<222> LOCATION: (66)..(67)
<223> OTHER INFORMATION: X=any amino acid
<220> FEATURE:
<221> NAME/KEY: MISC_FEATURE
<222> LOCATION: (69)..(94)
<223> OTHER INFORMATION: X=any amino acid
<220> FEATURE:
<221> NAME/KEY: MISC_FEATURE
<222> LOCATION: (96)..(97)
<223> OTHER INFORMATION: X=any amino acid
<220> FEATURE:
<221> NAME/KEY: MISC_FEATURE
<222> LOCATION: (99)..(101)
<223> OTHER INFORMATION: X=any amino acid

<400> SEQUENCE: 16

Arg Xaa Xaa Xaa Xaa Xaa Xaa Xaa Lys Xaa Xaa Glu Xaa Tyr Xaa Xaa
1               5                   10                  15

Xaa Xaa Xaa Xaa Xaa Xaa Xaa Xaa Xaa Xaa Xaa Xaa Xaa Xaa Xaa
        20                  25                  30
```

-continued

```
Gln Gln Xaa Xaa Xaa Xaa Xaa Xaa Xaa Xaa Xaa Xaa Xaa Xaa
        35              40              45

Xaa Xaa Asp Leu Xaa Xaa Pro Xaa Xaa Xaa Xaa Xaa Xaa Glu Xaa Asp
    50              55                      60

Glu Xaa Xaa His Xaa Xaa Xaa Xaa Xaa Xaa Xaa Xaa Xaa Xaa Xaa
65              70                      75                      80

Xaa Xaa Xaa Xaa Xaa Xaa Xaa Xaa Xaa Xaa Xaa Xaa Xaa Asp Xaa
            85                      90                  95

Xaa Arg Xaa Xaa Xaa Ile
                100
```